United States Patent
Drijfhout et al.

(10) Patent No.: US 7,993,869 B2
(45) Date of Patent: Aug. 9, 2011

(54) METHOD FOR DETECTING GLUTEN

(75) Inventors: Jan Wouter Drijfhout, Leiden (NL);
Frits Koning, Leiderdorp (NL);
Elisabeth Hermine Adriane Spaenij-Dekking, Leiden (NL)

(73) Assignee: Academisch Ziekenhuis Leiden, Leiden (NL)

( * ) Notice: Subject to any disclaimer, the term of this patent is extended or adjusted under 35 U.S.C. 154(b) by 888 days.

(21) Appl. No.: 11/630,818

(22) PCT Filed: Jun. 1, 2005

(86) PCT No.: PCT/NL2005/000400
§ 371 (c)(1),
(2), (4) Date: Nov. 7, 2007

(87) PCT Pub. No.: WO2006/004394
PCT Pub. Date: Jan. 12, 2006

(65) Prior Publication Data
US 2008/0152780 A1    Jun. 26, 2008

(30) Foreign Application Priority Data

Jun. 30, 2004 (EP) .................................. 04076902

(51) Int. Cl.
G01N 33/53 (2006.01)
G01N 33/531 (2006.01)
G01N 33/543 (2006.01)
G01N 33/563 (2006.01)

(52) U.S. Cl. ........... 435/7.93; 435/4; 435/7.1; 435/7.91; 435/7.92

(58) Field of Classification Search .................. None
See application file for complete search history.

(56) References Cited

U.S. PATENT DOCUMENTS
2007/0031399 A1* 2/2007 Edens et al. ............... 424/94.63

FOREIGN PATENT DOCUMENTS
EP    0 905 518 A1    3/1999
(Continued)

OTHER PUBLICATIONS
Written Opinion for PCT/NL2005/000400 dated Jan. 3, 2006.*
(Continued)

*Primary Examiner* — Unsu Jung
(74) *Attorney, Agent, or Firm* — Hoffmann & Baron, LLP

(57) ABSTRACT

Provided is a mAb-based method for the detection of T cell stimulatory epitopes known to be involved in CD. The method has many advantages compared to the existing methods for the detection of gluten since it is the first method that can; (i) detect T cell stimulatory epitopes of gluten; (ii) detect the epitopes separately, (iii) detect T cell stimulatory epitopes present on gliadin and glutenin homologues present in other cereals also known to be involved in CD; and (iv) detect T cell stimulatory epitopes on both intact proteins and small protein fragments. The new method is a valuable tool in the screening of basic ingredients, semi manufactured ingredients and food products that are intended to be used in the gluten free diet of CD patients. Moreover the new method can also be used for the screening of cereals and different wheat varieties for the level of toxicity for CD patients. Thereby the method can help in the selection of cereals and wheat varieties with low toxicity which might form the basis for future breeding programs. In the future these cereals will be used for the production of safe food for CD patients.

20 Claims, 10 Drawing Sheets

FOREIGN PATENT DOCUMENTS

Figure 1:
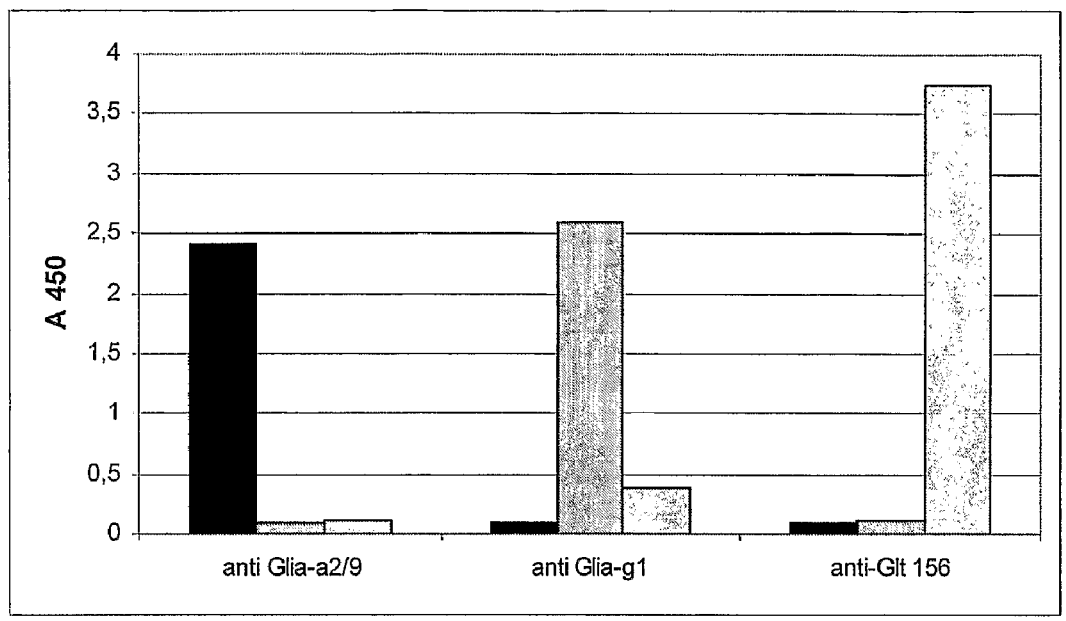

| WO | WO 97/09620 | 3/1997 |
|---|---|---|
| WO | WO 01/25793 A2 | 4/2001 |
| WO | WO 01/75451 A1 | 10/2001 |
| WO | WO 02/083722 A2 | 10/2002 |
| WO | WO 03/066079 A2 | 8/2003 |

OTHER PUBLICATIONS

Amanda S. Hill and John H. Skerritt, "Monoclonal Antibody Based Two-site Enzyme Immunoassays for Wheat Gluten Proteins. 1. Kinetic Characteristics and Comparison with Other ELISA Formats," *Food and Agricultural Immunology*, 1:147-160 (1989).

Spaenij-Dekking, et al., "A novel and sensitive method for the detection of T cell stimulatory epitopes of α/β- and γ-gliadin," www.gutjnl.com, Gut 2004;53:1267-1273.

Spaenij-Dekking, et al., Natural Variation in Toxicity of Wheat: Potential for Selection of Nontoxic Varieties for Celiac Disease Patients, *Gastroenterology*, 129:797-806 (2005).

Skerritt, et al., "Cellular and humoral responses in celiac disease. 2. Protein extracts from different cereals," *Clinica Chimica Acta*, 204:109-122 (1991).

Vader, et al., The Gluten Response in Children With Celiac Disease is Directed Toward Multiple Gliadin and Glutenin Peptides, *Gastroenterology*, 122:1729-1737 (2002).

Vader, et al. Characterization of Cereal Toxicity for Celiac Disease Patients Based on Protein Homology in Grains, *Gastroenterology*, 125:1105-1113 (2003).

Molberg, et al. Intestinal T-Cell Responses to High-Molecular-Weight Glutenins in Celiac Disease, *Gastroenterology*, 125:337-344 (2003).

Molberg, et al. Mapping of Gluten T-Cell Epitopes in the Bread Ancestors: Implications for Celiac Disease, *Gastroenterology*, 128:393:401 (2005).

*Triticum speltoides*, XP-002359265 (1964).

*Triticum aestivum* (Sappo), XP-002359266 (1969).

Yvonne Van De Wal et al., "Small Intestinal T Cells of Celiac Disease Patients Recognize a Natural Pepsin Fragment of Gliadin", Proc. Natl. Acad. Sci. USA, vol. 95, pp. 10050-10054, Aug. 1998.

Helene Arentz-Hansen et al., "The Intestinal T Cell Response to α-Gliadin in Adult Celiac Disease is Focused on a Single Deamidated Glutamine Targeted by Tissue Transglutaminase", J. Exp. Med., vol. 191, No. 4, pp. 603-612, Feb. 2000.

Oyvind Molberg et al., "Tissue Transglutaminase Selectively Modifies Gliadin Peptides That Are Recognized by Gut-Derived T Cells in Celiac Disease", Nature Medicine, vol. 4, No. 6, pp. 713-717, Jun. 1998.

Oyvind Molberg et al., "Intestinal T-Cell Responses to High-Molecular-Weight Glutenins in Celiac Disease", Gastroenterology, vol. 125, No. 2, pp. 337-344, 2003.

Burkhard Fleckenstein et al., "Gliadin T Cell Epitope Selection by Tissue Transglutaminase in Celiac Disease", The Journal of Biological Chemistry, vol. 277, No. 37, pp. 34109-34116, 2002.

Lu Shan et al., "Structural Basis for Gluten Intolerance in Celiac Spure", Science, vol. 297, pp. 2275-2279, 2002.

H. Sjostrom et al., "Identification of a Gliadin T-Cell Epitope in Coeliac Disease: General Importance of Gliadin Deamidation for Intestinal T-Cell Regognition", Scand. J. Immunol, vol. 48, pp. 111-115, 1998.

E H A Spaenij-Dekking et al., A Novel and Sensitive Method for the Detection of T Cell Stimulatory Epitopes of α/β- and γ-gliadin, Gut, vol. 53, pp. 1267-1273, 2004.

L. Willemijn Vader et al., "Characterization of Cereal Toxicity for Celiac Disease Patients Based on Protein Homology in Grains", Gastroenterology, vol. 125, pp. 1105-1113, 2003.

Willemijn Vader et al., "The Gluten Response in Children with Celiac Disease is Directed Toward Multiple Gliadin and Glutenin Peptides", Gastroenterology, vol. 122, pp. 1729-1737, 2002.

L. Willemijn Vader et al., "Specificity of Tissue Transglutaminase Explains Cereal Toxicity in Celiac Disease", J. Exp. Med., vol. 195, No. 5, pp. 643-649, 2002.

Yvonne Van De Wal, et al., "Glutenin is Involved in the Gluten-Driven Mucosal T Cell Response", Eur. J. Immunol., vol. 29, pp. 3133-3139, 1999.

Yvonne Van De Wal, et al., "Cutting Edge: Selective Deamidation by Tissue Transglutaminase Strongly Enhances Gliadin-Specific T Cell Reactivity", The Journal of Immunology, pp. 1585-1588, vol. 161, 1998.

*Triticum aestivum* group Compactum (Weissahr Rotkorn Binkel), XP-002359267 (Jun. 21, 2004).

* cited by examiner

A

B

C

D

```
                       SEQUENCE LISTING

<160> NUMBER OF SEQ ID NOS: 81

<210> SEQ ID NO 1
   <211> LENGTH: 15
   <212> TYPE: PRT
   <213> ORGANISM: Artificial
   <220> FEATURE:
   <223> OTHER INFORMATION: alfa-gliadin T-cell epitope

<400> SEQUENCE: 1

Gln Leu Gln Pro Phe Pro Gln Pro Gln Leu Pro Tyr Pro Gln Pro
   1               5                   10                  15

<210> SEQ ID NO 2
   <211> LENGTH: 12
   <212> TYPE: PRT
   <213> ORGANISM: Artificial
   <220> FEATURE:
   <223> OTHER INFORMATION: alfa-gliadin T-cell epitope
   <220> FEATURE:
   <221> NAME/KEY: MISC_FEATURE
   <222> LOCATION: (1)..(1)
   <223> OTHER INFORMATION: "Xaa" can be any amino acid

<400> SEQUENCE: 2

Xaa Gln Pro Phe Pro Gln Pro Gln Leu Pro Tyr Pro
   1               5                   10

<210> SEQ ID NO 3
   <211> LENGTH: 8
   <212> TYPE: PRT
   <213> ORGANISM: Artificial
   <220> FEATURE:
   <223> OTHER INFORMATION: alfa-gliadin T-cell epitope
   <220> FEATURE:
   <221> NAME/KEY: MISC_FEATURE
   <222> LOCATION: (1)..(1)
   <223> OTHER INFORMATION: "Xaa" can be any amino acid

<400> SEQUENCE: 3

Xaa Gln Pro Phe Pro Gln Pro Gln
   1               5

<210> SEQ ID NO 4
   <211> LENGTH: 22
   <212> TYPE: PRT
   <213> ORGANISM: Artificial
   <220> FEATURE:
   <223> OTHER INFORMATION: gluten epitope

<400> SEQUENCE: 4

Gln Pro Gln Gln Pro Gln Gln Ser Phe Pro Gln Gln Arg Pro Phe
   1               5                   10                  15

Ile Gln Pro Ser Leu Gln
                   20

<210> SEQ ID NO 5
```

```
<211> LENGTH: 6
<212> TYPE: PRT
<213> ORGANISM: Artificial
<220> FEATURE:
<223> OTHER INFORMATION: gluten epitope

<400> SEQUENCE: 5

Gln Gln Arg Pro Phe Ile
1               5

<210> SEQ ID NO 6
<211> LENGTH: 14
<212> TYPE: PRT
<213> ORGANISM: Artificial
<220> FEATURE:
<223> OTHER INFORMATION: gluten epitope

<400> SEQUENCE: 6

Gln Pro Pro Phe Ser Gln Gln Gln Ser Pro Phe Ser Gln
1               5                   10

<210> SEQ ID NO 7
<211> LENGTH: 6
<212> TYPE: PRT
<213> ORGANISM: Artificial
<220> FEATURE:
<223> OTHER INFORMATION: gluten epitope

<400> SEQUENCE: 7

Pro Pro Phe Ser Gln Gln
1               5

<210> SEQ ID NO 8
<211> LENGTH: 5
<212> TYPE: PRT
<213> ORGANISM: Artificial
<220> FEATURE:
<223> OTHER INFORMATION: gluten epitope

<400> SEQUENCE: 8

Gln Ser Pro Phe Ser
1               5

<210> SEQ ID NO 9
<211> LENGTH: 16
<212> TYPE: PRT
<213> ORGANISM: Artificial
<220> FEATURE:
<223> OTHER INFORMATION: gluten epitope

<400> SEQUENCE: 9

Pro Gly Gln Gly Gln Gln Gly Tyr Tyr Pro Thr Ser Leu Gln Gln Pro
1               5                   10                  15

<210> SEQ ID NO 10
<211> LENGTH: 16
<212> TYPE: PRT
<213> ORGANISM: Artificial
<220> FEATURE:
<223> OTHER INFORMATION: gluten epeitope

<400> SEQUENCE: 10

Pro Gly Gln Gly Gln Gln Gly Tyr Tyr Pro Thr Ser Gln Gln Gln Pro
1               5                   10                  15

<210> SEQ ID NO 11
<211> LENGTH: 16
<212> TYPE: PRT
```

```
<213> ORGANISM: Artificial
<220> FEATURE:
<223> OTHER INFORMATION: gluten epitope

<400> SEQUENCE: 11

Pro Gly Gln Gly Gln Pro Gly Tyr Tyr Pro Thr Ser Leu Gln Gln Pro
1               5                   10                  15

<210> SEQ ID NO 12
<211> LENGTH: 16
<212> TYPE: PRT
<213> ORGANISM: Artificial
<220> FEATURE:
<223> OTHER INFORMATION: gluten epitope

<400> SEQUENCE: 12

Pro Gly Gln Gly Gln Pro Gly Tyr Tyr Pro Thr Ser Gln Gln Gln Pro
1               5                   10                  15

<210> SEQ ID NO 13
<211> LENGTH: 14
<212> TYPE: PRT
<213> ORGANISM: Artificial
<220> FEATURE:
<223> OTHER INFORMATION: gluten epitope

<400> SEQUENCE: 13

Gln Gly Gln Gln Gly Tyr Tyr Pro Thr Ser Pro Gln Gln Pro
1               5                   10

<210> SEQ ID NO 14
<211> LENGTH: 14
<212> TYPE: PRT
<213> ORGANISM: Artificial
<220> FEATURE:
<223> OTHER INFORMATION: gluten epitope

<400> SEQUENCE: 14

Gln Gly Gln Gln Gly Tyr Tyr Pro Thr Ser Pro Gln Gln Ser
1               5                   10

<210> SEQ ID NO 15
<211> LENGTH: 13
<212> TYPE: PRT
<213> ORGANISM: Artificial
<220> FEATURE:
<223> OTHER INFORMATION: synthetic T cell epitope peptide

<400> SEQUENCE: 15

Gln Pro Phe Pro Gln Pro Gln Leu Pro Tyr Pro Gln Pro
1               5                   10

<210> SEQ ID NO 16
<211> LENGTH: 17
<212> TYPE: PRT
<213> ORGANISM: Artificial
<220> FEATURE:
<223> OTHER INFORMATION: synthetic T cell epitope peptide

<400> SEQUENCE: 16

Pro Gln Gln Ser Phe Pro Gln Gln Gln Arg Pro Phe Ile Gln Pro Ser
1               5                   10                  15

Leu

<210> SEQ ID NO 17
<211> LENGTH: 12
<212> TYPE: PRT
```

```
<213> ORGANISM: Artificial
<220> FEATURE:
<223> OTHER INFORMATION: synthetic T cell epitope peptide

<400> SEQUENCE: 17

Pro Pro Phe Ser Gln Gln Gln Gln Ser Pro Phe Ser
1               5                   10

<210> SEQ ID NO 18
<211> LENGTH: 16
<212> TYPE: PRT
<213> ORGANISM: Artificial
<220> FEATURE:
<223> OTHER INFORMATION: synthetic T cell epitope peptide
<220> FEATURE:
<221> NAME/KEY: MISC_FEATURE
<222> LOCATION: (6)..(6)
<223> OTHER INFORMATION: "Xaa" can be Q/P"
<220> FEATURE:
<221> NAME/KEY: MISC_FEATURE
<222> LOCATION: (13)..(13)
<223> OTHER INFORMATION: "Xaa" can be L/Q

<400> SEQUENCE: 18

Pro Gly Gln Gly Gln Xaa Gly Tyr Tyr Pro Thr Ser Xaa Gln Gln Pro
1               5                   10                  15

<210> SEQ ID NO 19
<211> LENGTH: 14
<212> TYPE: PRT
<213> ORGANISM: Artificial
<220> FEATURE:
<223> OTHER INFORMATION: synthetic T cell epitope peptide
<220> FEATURE:
<221> NAME/KEY: MISC_FEATURE
<222> LOCATION: (14)..(14)
<223> OTHER INFORMATION: "Xaa" can be P/S

<400> SEQUENCE: 19

Gln Gly Gln Gln Gly Tyr Tyr Pro Thr Ser Pro Gln Gln Xaa
1               5                   10

<210> SEQ ID NO 20
<211> LENGTH: 8
<212> TYPE: PRT
<213> ORGANISM: Artificial
<220> FEATURE:
<223> OTHER INFORMATION: minimal amino acid sequence recognized by
      anti-Glia-alfa2/9 mAb

<400> SEQUENCE: 20

Leu Gln Pro Phe Pro Gln Pro Gln
1               5

<210> SEQ ID NO 21
<211> LENGTH: 6
<212> TYPE: PRT
<213> ORGANISM: Artificial
<220> FEATURE:
<223> OTHER INFORMATION: minimal amino acid sequence recognized by
      anti-Glia-gamma1 mAb

<400> SEQUENCE: 21

Gln Gln Arg Pro Phe Ile
1               5

<210> SEQ ID NO 22
<211> LENGTH: 5
<212> TYPE: PRT
<213> ORGANISM: Artificial
```

```
<220> FEATURE:
<223> OTHER INFORMATION: minimal amino acid sequence recognized by
      anti-LMW-glutenin-1 mAb

<400> SEQUENCE: 22

Gln Ser Pro Phe Ser
1               5

<210> SEQ ID NO 23
<211> LENGTH: 16
<212> TYPE: PRT
<213> ORGANISM: Artificial
<220> FEATURE:
<223> OTHER INFORMATION: LMW glutenin epitope for vaccination
<220> FEATURE:
<221> NAME/KEY: MISC_FEATURE
<222> LOCATION: (4)..(4)
<223> OTHER INFORMATION: "Xaa" stands for aminohexanoyl spacer

<400> SEQUENCE: 23

Asp Asp Asp Xaa Pro Pro Phe Ser Gln Gln Gln Gln Ser Pro Phe Ser
1               5                   10                  15

<210> SEQ ID NO 24
<211> LENGTH: 20
<212> TYPE: PRT
<213> ORGANISM: Artificial
<220> FEATURE:
<223> OTHER INFORMATION: HMW glutenin epitope for vaccination
<220> FEATURE:
<221> NAME/KEY: MISC_FEATURE
<222> LOCATION: (4)..(4)
<223> OTHER INFORMATION: "Xaa" stands for aminohexanoyl spacer
<220> FEATURE:
<221> NAME/KEY: MISC_FEATURE
<222> LOCATION: (10)..(10)
<223> OTHER INFORMATION: "Xaa" stands for Q/P
<220> FEATURE:
<221> NAME/KEY: MISC_FEATURE
<222> LOCATION: (17)..(17)
<223> OTHER INFORMATION: "Xaa" stands for L/Q

<400> SEQUENCE: 24

Asp Asp Asp Xaa Pro Gly Gln Gly Gln Xaa Gly Tyr Tyr Pro Thr Ser
1               5                   10                  15

Xaa Gln Gln Pro
            20

<210> SEQ ID NO 25
<211> LENGTH: 18
<212> TYPE: PRT
<213> ORGANISM: Artificial
<220> FEATURE:
<223> OTHER INFORMATION: HMW glutenin epitope for vaccination
<220> FEATURE:
<221> NAME/KEY: MISC_FEATURE
<222> LOCATION: (4)..(4)
<223> OTHER INFORMATION: "Xaa" stands for aminohexanoyl spacer
<220> FEATURE:
<221> NAME/KEY: MISC_FEATURE
<222> LOCATION: (18)..(18)
<223> OTHER INFORMATION: "Xaa" stands for P/S

<400> SEQUENCE: 25

Asp Asp Asp Xaa Gln Gly Gln Gln Gly Tyr Tyr Pro Thr Ser Pro Gln
1               5                   10                  15

Gln Xaa

<210> SEQ ID NO 26
<211> LENGTH: 20
```

```
<212> TYPE: PRT
<213> ORGANISM: Artificial
<220> FEATURE:
<223> OTHER INFORMATION: LMW-Glt-156 T cell epitope containing peptide
      (biotinylated)
<220> FEATURE:
<221> NAME/KEY: MISC_FEATURE
<222> LOCATION: (1)..(8)
<223> OTHER INFORMATION: "Xaa" on pos. 1 and 8 stands for aminohexanoyl
      spacer

<400> SEQUENCE: 26

Xaa Lys Ala Lys Ala Lys Ala Xaa Pro Pro Phe Ser Gln Gln Gln Gln
1               5                   10                  15

Ser Pro Phe Ser
            20

<210> SEQ ID NO 27
<211> LENGTH: 24
<212> TYPE: PRT
<213> ORGANISM: Artificial
<220> FEATURE:
<223> OTHER INFORMATION: biotinylated peptide containing HMW gltenin
      epitope
<220> FEATURE:
<221> NAME/KEY: MISC_FEATURE
<222> LOCATION: (1)..(10)
<223> OTHER INFORMATION: "Xaa" on pos. 1 and 10 stands for aminohexanoyl
      spacer

<400> SEQUENCE: 27

Xaa Lys Ala Lys Ala Lys Ala Lys Ala Xaa Gln Gly Gln Gln Gly Tyr
1               5                   10                  15

Tyr Pro Thr Ser Pro Gln Gln Pro
            20

<210> SEQ ID NO 28
<211> LENGTH: 14
<212> TYPE: PRT
<213> ORGANISM: Artificial
<220> FEATURE:
<223> OTHER INFORMATION: peptide with epitope Glia-alfa2/alfa9 (61-71)
<220> FEATURE:
<221> NAME/KEY: MISC_FEATURE
<222> LOCATION: (4)..(4)
<223> OTHER INFORMATION: "Xaa" stands for aminohexanoyl spacer

<400> SEQUENCE: 28

Asp Asp Asp Xaa Phe Pro Gln Pro Leu Pro Tyr Pro Gln Pro
1               5                   10

<210> SEQ ID NO 29
<211> LENGTH: 15
<212> TYPE: PRT
<213> ORGANISM: Artificial
<220> FEATURE:
<223> OTHER INFORMATION: peptide with epitope Glia-alfa2/alfa9 (59-69)
<220> FEATURE:
<221> NAME/KEY: MISC_FEATURE
<222> LOCATION: (4)..(4)
<223> OTHER INFORMATION: "Xaa" stands for aminohexanoyl spacer

<400> SEQUENCE: 29

Asp Asp Asp Xaa Gln Pro Phe Pro Gln Pro Gln Leu Pro Tyr Pro
1               5                   10                  15

<210> SEQ ID NO 30
<211> LENGTH: 16
<212> TYPE: PRT
<213> ORGANISM: Artificial
```

-continued

```
<220> FEATURE:
<223> OTHER INFORMATION: peptide with epitope Glia-alfa2/alfa9 (61-71)

<400> SEQUENCE: 30

Arg Gly Arg Gly Arg Phe Pro Gln Pro Gln Leu Pro Tyr Pro Gln Pro
1               5                   10                  15

<210> SEQ ID NO 31
<211> LENGTH: 16
<212> TYPE: PRT
<213> ORGANISM: Artificial
<220> FEATURE:
<223> OTHER INFORMATION: peptide with epitope Glia-alfa2/alfa9 (59-69)

<400> SEQUENCE: 31

Arg Gly Arg Gly Arg Gln Pro Phe Pro Gln Pro Gln Leu Pro Tyr Pro
1               5                   10                  15

<210> SEQ ID NO 32
<211> LENGTH: 16
<212> TYPE: PRT
<213> ORGANISM: Artificial
<220> FEATURE:
<223> OTHER INFORMATION: peptide with epitope Glia-gamma1 (142-153)
<220> FEATURE:
<221> NAME/KEY: MISC_FEATURE
<222> LOCATION: (4)..(4)
<223> OTHER INFORMATION: "Xaa" stands for aminohexanoyl spacer

<400> SEQUENCE: 32

Asp Asp Asp Xaa Pro Gln Gln Ser Phe Pro Gln Gln Gln Arg Pro Phe
1               5                   10                  15

<210> SEQ ID NO 33
<211> LENGTH: 16
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (4)..(4)
<223> OTHER INFORMATION: "Xaa" stands for aminohexanoyl spacer

<400> SEQUENCE: 33

Asp Asp Asp Xaa Pro Gln Gln Gln Arg Pro Phe Ile Gln Pro Ser Leu
1               5                   10                  15

<210> SEQ ID NO 34
<211> LENGTH: 15
<212> TYPE: PRT
<213> ORGANISM: Artificial
<220> FEATURE:
<223> OTHER INFORMATION: peptide with epitope Glia-gamma1 (149-159)
<220> FEATURE:
<221> NAME/KEY: MISC_FEATURE
<222> LOCATION: (4)..(4)
<223> OTHER INFORMATION: "Xaa" stands for aminohexanoyl spacer

<400> SEQUENCE: 34

Asp Asp Asp Xaa Gln Gln Arg Pro Phe Ile Gln Pro Ser Leu Gln
1               5                   10                  15

<210> SEQ ID NO 35
<211> LENGTH: 23
<212> TYPE: PRT
<213> ORGANISM: Artificial
<220> FEATURE:
<223> OTHER INFORMATION: peptide with epitope Glia-gamma1 (142-159)
<220> FEATURE:
```

```
<221> NAME/KEY: MISC_FEATURE
<222> LOCATION: (4)..(4)
<223> OTHER INFORMATION: "Xaa" stands for aminohexanoyl spacer

<400> SEQUENCE: 35

Arg Gly Arg Gly Arg Pro Gln Gln Ser Phe Pro Gln Gln Gln Arg Pro
1               5                   10                  15

Phe Ile Gln Pro Ser Leu Gln
            20

<210> SEQ ID NO 36
<211> LENGTH: 17
<212> TYPE: PRT
<213> ORGANISM: Artificial
<220> FEATURE:
<223> OTHER INFORMATION: peptide with epitope Glt-156 (41-58)

<400> SEQUENCE: 36

Arg Gly Arg Gly Arg Pro Pro Phe Ser Gln Gln Gln Gln Ser Pro Phe
1               5                   10                  15

Ser

<210> SEQ ID NO 37
<211> LENGTH: 23
<212> TYPE: PRT
<213> ORGANISM: Artificial
<220> FEATURE:
<223> OTHER INFORMATION: biotinylated competitor peptide Glia alfa2/9
<220> FEATURE:
<221> NAME/KEY: MISC_FEATURE
<222> LOCATION: (1)..(10)
<223> OTHER INFORMATION: "Xaa" on pos. 1 and 10 stands for aminohexanoyl
      spacer

<400> SEQUENCE: 37

Xaa Lys Ala Lys Ala Lys Ala Lys Ala Xaa Gln Pro Phe Pro Gln Pro
1               5                   10                  15

Gln Leu Pro Tyr Pro Gln Pro
            20

<210> SEQ ID NO 38
<211> LENGTH: 28
<212> TYPE: PRT
<213> ORGANISM: Artificial
<220> FEATURE:
<223> OTHER INFORMATION: biotinylated competitor peptide Glia gamma1
<220> FEATURE:
<221> NAME/KEY: MISC_FEATURE
<222> LOCATION: (1)..(10)
<223> OTHER INFORMATION: "Xaa" on pos. 1 and 10 stands for aminohexanoyl
      spacer

<400> SEQUENCE: 38

Xaa Ala Lys Ala Lys Ala Lys Ala Lys Xaa Pro Gln Gln Ser Phe Pro
1               5                   10                  15

Gln Gln Gln Arg Pro Phe Ile Gln Pro Ser Leu Gln
            20                  25

<210> SEQ ID NO 39
<211> LENGTH: 20
<212> TYPE: PRT
<213> ORGANISM: Artificial
<220> FEATURE:
<223> OTHER INFORMATION: biotinylated competitor peptide Glt-156
<220> FEATURE:
<221> NAME/KEY: MISC_FEATURE
<222> LOCATION: (1)..(1)
<223> OTHER INFORMATION: "Xaa" stands for aminohexanoyl spacer
```

<400> SEQUENCE: 39

Xaa Lys Ala Lys Ala Lys Ala Glx Pro Pro Phe Ser Gln Gln Gln Gln
1               5                   10                  15

Ser Pro Phe Ser
            20

<210> SEQ ID NO 40
<211> LENGTH: 139
<212> TYPE: PRT
<213> ORGANISM: Artificial
<220> FEATURE:
<223> OTHER INFORMATION: anti-alpha-gliadin

<400> SEQUENCE: 40

Met Asn Leu Gly Leu Asn Trp Ile Phe Leu Val Leu Val Leu Lys Gly
1               5                   10                  15

Val Gln Cys Glu Val Lys Leu Val Glu Ser Gly Gly Gly Leu Val Lys
            20                  25                  30

Pro Gly Gly Ser Leu Lys Leu Ser Cys Ala Ala Ser Gly Phe Thr Phe
        35                  40                  45

Ser Thr Tyr Ala Met Ser Trp Val Arg Gln Thr Pro Glu Lys Arg Leu
50                  55                  60

Glu Trp Val Ala Ser Ile Ser Ser Gly Gly Ser Thr Thr Tyr Tyr Pro
65                  70                  75                  80

Asp Ser Val Lys Gly Arg Phe Thr Ile Ser Arg Asp Asn Ala Arg Asn
                85                  90                  95

Ile Leu Tyr Leu Gln Met Ser Ser Leu Arg Ser Glu Asp Thr Ala Met
            100                 105                 110

Tyr Tyr Cys Ala Arg Val Pro Thr Tyr Lys Asp Tyr Ala Met Asp Tyr
        115                 120                 125

Trp Gly Gln Gly Thr Ser Val Thr Val Ser Ser
    130                 135

<210> SEQ ID NO 41
<211> LENGTH: 139
<212> TYPE: PRT
<213> ORGANISM: Artificial
<220> FEATURE:
<223> OTHER INFORMATION: anti-gamma-gliadin

<400> SEQUENCE: 41

Met Asp Trp Val Trp Asn Leu Pro Phe Leu Met Ala Ala Ala Gln Ser
1               5                   10                  15

Ala Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
        35                  40                  45

Thr Asn Tyr Gly Met Asn Trp Val Lys Gln Ala Pro Gly Lys Gly Leu
    50                  55                  60

Lys Trp Met Gly Trp Ile Asn Thr Tyr Thr Gly Glu Pro Thr Tyr Ala
65                  70                  75                  80

Asp Asp Phe Lys Gly Arg Phe Ala Phe Ser Leu Glu Ile Ser Ala Ser
                85                  90                  95

Thr Ala Tyr Leu Gln Ile Asn Asn Leu Lys Asn Glu Asp Met Ala Thr
            100                 105                 110

Tyr Phe Cys Ala Lys Thr Ala Thr Tyr Tyr Ala Met Asp Tyr Trp Gly
        115                 120                 125

```
Gln Gly Thr Ser Val Thr Ala Ala Lys Thr
        130                 135

<210> SEQ ID NO 42
<211> LENGTH: 150
<212> TYPE: PRT
<213> ORGANISM: Artificial
<220> FEATURE:
<223> OTHER INFORMATION: anti-LMW-glu1
<220> FEATURE:
<221> NAME/KEY: MISC_FEATURE
<222> LOCATION: (6)..(143)
<223> OTHER INFORMATION: "Xaa" on pos. 6, 8 and 143 is unknown

<400> SEQUENCE: 42

Met Asp Trp Val Trp Xaa Leu Xaa Phe Leu Met Ala Ala Gln Ser
1               5                   10                  15

Ile Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
        35                  40                  45

Thr Asn Tyr Gly Met Asn Trp Val Lys Gln Ala Pro Gly Lys Gly Leu
    50                  55                  60

Lys Trp Met Gly Trp Ile Asn Thr Asn Thr Gly Glu Pro Ala Tyr Ala
65                  70                  75                  80

Glu Glu Phe Lys Gly Arg Phe Ala Phe Ser Leu Glu Thr Ser Ala Ser
                85                  90                  95

Thr Ala Tyr Leu Gln Ile Asn Asn Leu Lys Asn Glu Asp Thr Ala Thr
            100                 105                 110

Tyr Phe Cys Ala Arg Ser Gly Tyr Tyr Pro Phe Ala Tyr Trp Gly Gln
        115                 120                 125

Gln Thr Leu Val Thr Val Ser Ala Ala Thr Thr Thr Ala Pro Xaa Val
    130                 135                 140

Pro Leu Ala Pro Gly Ser
145                 150

<210> SEQ ID NO 43
<211> LENGTH: 149
<212> TYPE: PRT
<213> ORGANISM: Artificial
<220> FEATURE:
<223> OTHER INFORMATION: anti-LMW-glu2

<400> SEQUENCE: 43

Met Asp Trp Val Trp Asn Leu Leu Phe Leu Met Ala Ala Gln Thr
1               5                   10                  15

Ile Gln Ala Gln Ile Gln Leu Val Gln Ser Gly Pro Glu Met Lys Lys
            20                  25                  30

Pro Gly Glu Thr Val Lys Ile Ser Cys Lys Ala Ser Gly Tyr Thr Phe
        35                  40                  45

Thr Asp Tyr Ser Met His Trp Val Lys Glu Ala Pro Gly Lys Gly Leu
    50                  55                  60

Lys Trp Met Gly Trp Ile Asn Thr Glu Thr Ala Lys Pro Thr Tyr Ala
65                  70                  75                  80

Asp Asp Phe Arg Gly Arg Phe Ala Phe Ser Leu Glu Thr Ser Ala Ser
                85                  90                  95

Thr Ala Tyr Leu Gln Ile Asn Asn Leu Lys Asn Glu Asp Thr Ala Thr
            100                 105                 110

Tyr Phe Cys Ser Arg Gly Ile Arg Asp Tyr Phe Asp Tyr Trp Gly Gln
        115                 120                 125
```

```
Gly Thr Thr Leu Thr Val Ser Ser Ala Lys Thr Thr Pro Pro Val
    130                 135                 140

Tyr Pro Leu Ala Pro
145

<210> SEQ ID NO 44
<211> LENGTH: 152
<212> TYPE: PRT
<213> ORGANISM: Artificial
<220> FEATURE:
<223> OTHER INFORMATION: anti-HMW

<400> SEQUENCE: 44

Met Tyr Leu Gly Leu Ser Cys Val Ile Phe Ile Val Phe Leu Leu Lys
1               5                   10                  15

Gly Val Gln Ser Glu Leu Lys Leu Glu Ser Gly Gly Asn Leu Val
            20                  25                  30

Gln Pro Gly Gly Ser Leu Lys Leu Ser Cys Leu Ala Ser Gly Phe Ser
        35                  40                  45

Phe Thr Lys Tyr Trp Met Asn Trp Val Arg Gln Ser Pro Glu Arg Gly
50                  55                  60

Leu Glu Trp Val Gly Glu Ile Arg Ser Lys Ser Asp Asp Tyr Ala Thr
65                  70                  75                  80

His Tyr Ala Glu Ser Val Arg Gly Arg Phe Thr Ile Ser Arg Asp Asp
                85                  90                  95

Ser Lys Ser Ser Val Tyr Leu Gln Met Asn Asn Leu Arg Pro Glu Asp
            100                 105                 110

Ala Gly Ile Tyr Tyr Cys Ser Ser Gly Thr Arg Gly Tyr Trp Gly Gln
        115                 120                 125

Gly Thr Thr Leu Thr Val Ser Ser Ala Lys Thr Thr Pro Pro Ser Val
    130                 135                 140

Tyr Pro Leu Ala Pro Gly Ser Leu
145                 150

<210> SEQ ID NO 45
<211> LENGTH: 112
<212> TYPE: PRT
<213> ORGANISM: Artificial
<220> FEATURE:
<223> OTHER INFORMATION: anti-alpha-gliadin

<400> SEQUENCE: 45

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Leu Thr Phe Gly Ala Gly Thr Lys Leu Glu Leu Lys Arg
            100                 105                 110

<210> SEQ ID NO 46
```

```
<211> LENGTH: 108
<212> TYPE: PRT
<213> ORGANISM: Artificial
<220> FEATURE:
<223> OTHER INFORMATION: anti-gamma-gliadin

<400> SEQUENCE: 46

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Ile Leu Val
        35                  40                  45

Tyr Asp Ala Lys Thr Leu Ala Asp Ala Val Pro Ser Arg Phe Ser Gly
    50                  55                  60

Ser Gly Ser Gly Thr His Phe Ser Leu Lys Ile Asn Ser Leu Gln Pro
65                  70                  75                  80

Glu Asp Phe Gly Ser Tyr Tyr Cys Gln His His Tyr Gly Ser Pro Leu
                85                  90                  95

Thr Phe Gly Ala Gly Thr Lys Leu Glu Leu Lys Arg
            100                 105

<210> SEQ ID NO 47
<211> LENGTH: 107
<212> TYPE: PRT
<213> ORGANISM: Artificial
<220> FEATURE:
<223> OTHER INFORMATION: anti-LMW-glu1

<400> SEQUENCE: 47

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Asp Ile Gly Ser Ser
            20                  25                  30

Leu Asn Trp Leu Gln Gln Glu Pro Asp Gly Thr Ile Lys Arg Leu Ile
        35                  40                  45

Tyr Ala Thr Ser Ser Leu Asp Gly Val Pro Lys Arg Phe Ser Gly Ser
    50                  55                  60

Arg Ser Gly Ser Asp Tyr Ser Leu Thr Ile Ser Ser Leu Glu Ser Glu
65                  70                  75                  80

Asp Phe Val Asp Tyr Tyr Cys Leu Gln Tyr Ala Ser Ser Pro Val Thr
                85                  90                  95

Phe Gly Ala Gly Thr Lys Leu Glu Leu Lys Arg
            100                 105

<210> SEQ ID NO 48
<211> LENGTH: 112
<212> TYPE: PRT
<213> ORGANISM: Artificial
<220> FEATURE:
<223> OTHER INFORMATION: anti-LMW-glu2

<400> SEQUENCE: 48

Asp Ile Val Leu Thr Gln Ser Pro Ala Ser Leu Ala Val Ser Leu Gly
1               5                   10                  15

Gln Arg Ala Pro Ile Ser Cys Arg Ala Ser Lys Ser Val Ser Lys Ser
            20                  25                  30

Gly Tyr Asn Tyr Met His Trp Tyr Gln Gln Lys Pro Gly Gln Pro Pro
        35                  40                  45

Lys Leu Leu Ile Tyr Leu Ala Ser Asn Leu Gln Ser Gly Val Pro Ala
```

```
                      50                  55                  60
Arg Phe Ser Gly Ser Gly Ser Gly Thr Glu Phe Thr Leu Asp Ile His
 65                  70                  75                  80

Pro Val Glu Glu Glu Asp Ala Ala Thr Tyr Tyr Cys Gln His Ser Arg
                     85                  90                  95

Glu Leu Pro Phe Thr Phe Gly Ser Gly Thr Lys Leu Glu Ile Lys Arg
                100                 105                 110

<210> SEQ ID NO 49
<211> LENGTH: 110
<212> TYPE: PRT
<213> ORGANISM: Artificial
<220> FEATURE:
<223> OTHER INFORMATION: anti-HMW

<400> SEQUENCE: 49

His Val Val Met Thr Gln Ala Pro Leu Ser Leu Pro Val Ser Leu Gly
  1               5                  10                  15

Asp Gln Val Ser Ile Ser Cys Ser Thr Gln Ser Leu Val Ser Asp Gly
                 20                  25                  30

Asp Thr Phe Leu Asn Trp Cys Leu Gln Lys Pro Gly Gln Ser Pro Asn
             35                  40                  45

Leu Leu Ile Tyr Lys Val Ser Ser Arg Phe Ala Gly Val Pro Asp Arg
 50                  55                  60

Phe Thr Gly Ser Gly Ser Gly Thr Asp Phe Thr Leu Lys Ile Ser Arg
 65                  70                  75                  80

Val Glu Thr Glu Asp Leu Arg Val Val Phe Ser Gln Ser Ser Leu Val
                 85                  90                  95

Pro Arg Thr Phe Gly Gly Gly Thr Lys Leu Val Ile Thr Arg
                100                 105                 110

<210> SEQ ID NO 50
<211> LENGTH: 9
<212> TYPE: PRT
<213> ORGANISM: Artificial
<220> FEATURE:
<223> OTHER INFORMATION: alfa-gliadin epitope

<400> SEQUENCE: 50

Gln Gly Ser Phe Gln Pro Ser Gln Gln
  1               5

<210> SEQ ID NO 51
<211> LENGTH: 9
<212> TYPE: PRT
<213> ORGANISM: Artificial
<220> FEATURE:
<223> OTHER INFORMATION: HMW-glutenin eptiope

<400> SEQUENCE: 51

Gln Gly Tyr Tyr Pro Thr Ser Pro Gln
  1               5

<210> SEQ ID NO 52
<211> LENGTH: 9
<212> TYPE: PRT
<213> ORGANISM: Artificial
<220> FEATURE:
<223> OTHER INFORMATION: alfa-gliadin epitope

<400> SEQUENCE: 52

Pro Phe Pro Gln Pro Gln Leu Pro Tyr
  1               5
```

```
<210> SEQ ID NO 53
<211> LENGTH: 9
<212> TYPE: PRT
<213> ORGANISM: Artificial
<220> FEATURE:
<223> OTHER INFORMATION: alfa-gliadin epitope

<400> SEQUENCE: 53

Pro Gln Pro Gln Leu Pro Tyr Pro Gln
1               5

<210> SEQ ID NO 54
<211> LENGTH: 9
<212> TYPE: PRT
<213> ORGANISM: Artificial
<220> FEATURE:
<223> OTHER INFORMATION: alfa-gliadin epitope

<400> SEQUENCE: 54

Phe Arg Pro Gln Gln Pro Tyr Pro Gln
1               5

<210> SEQ ID NO 55
<211> LENGTH: 9
<212> TYPE: PRT
<213> ORGANISM: Artificial
<220> FEATURE:
<223> OTHER INFORMATION: gamma-gliadin epitope

<400> SEQUENCE: 55

Pro Gln Gln Ser Phe Pro Gln Gln Gln
1               5

<210> SEQ ID NO 56
<211> LENGTH: 9
<212> TYPE: PRT
<213> ORGANISM: Artificial
<220> FEATURE:
<223> OTHER INFORMATION: gamma-gliadin epitope

<400> SEQUENCE: 56

Phe Pro Gln Gln Pro Gln Gln Pro Phe
1               5

<210> SEQ ID NO 57
<211> LENGTH: 9
<212> TYPE: PRT
<213> ORGANISM: Artificial
<220> FEATURE:
<223> OTHER INFORMATION: gamma-gliadin epitope

<400> SEQUENCE: 57

Ile Gln Pro Gln Gln Pro Ala Gln Leu
1               5

<210> SEQ ID NO 58
<211> LENGTH: 9
<212> TYPE: PRT
<213> ORGANISM: Artificial
<220> FEATURE:
<223> OTHER INFORMATION: LMW-glutenin epitope

<400> SEQUENCE: 58

Phe Ser Gln Gln Gln Gln Ser Pro Phe
1               5
```

```
<210> SEQ ID NO 59
<211> LENGTH: 9
<212> TYPE: PRT
<213> ORGANISM: Artificial
<220> FEATURE:
<223> OTHER INFORMATION: LMW-glutenin epitope

<400> SEQUENCE: 59

Phe Ser Gln Gln Gln Gln Gln Pro Leu
1               5

<210> SEQ ID NO 60
<211> LENGTH: 9
<212> TYPE: PRT
<213> ORGANISM: Artificial
<220> FEATURE:
<223> OTHER INFORMATION: LMW-glutenin epitope
<220> FEATURE:
<221> NAME/KEY: misc_feature
<222> LOCATION: (2)..(2)
<223> OTHER INFORMATION: Xaa can be any naturally occurring amino acid

<400> SEQUENCE: 60

Gln Xaa Pro Gln Gln Pro Gln Gln Phe
1               5

<210> SEQ ID NO 61
<211> LENGTH: 10
<212> TYPE: PRT
<213> ORGANISM: Artificial
<220> FEATURE:
<223> OTHER INFORMATION: minimal eptiope for anti-Glia-alfa2/9 mAb

<400> SEQUENCE: 61

Tyr Leu Gln Leu Gln Pro Phe Pro Gln Pro
1               5                   10

<210> SEQ ID NO 62
<211> LENGTH: 9
<212> TYPE: PRT
<213> ORGANISM: Artificial
<220> FEATURE:
<223> OTHER INFORMATION: minimal eptiope for anti-Glia-alfa2/9 mAb

<400> SEQUENCE: 62

Gln Leu Gln Pro Phe Pro Gln Pro Gln
1               5

<210> SEQ ID NO 63
<211> LENGTH: 11
<212> TYPE: PRT
<213> ORGANISM: Artificial
<220> FEATURE:
<223> OTHER INFORMATION: minimal eptiope for anti-Glia-alfa2/9 mAb

<400> SEQUENCE: 63

Gln Leu Gln Pro Phe Pro Gln Leu Gln Leu Pro
1               5                   10

<210> SEQ ID NO 64
<211> LENGTH: 12
<212> TYPE: PRT
<213> ORGANISM: Artificial
<220> FEATURE:
<223> OTHER INFORMATION: minimal eptiope for anti-Glia-alfa2/9 mAb

<400> SEQUENCE: 64

Gln Leu Gln Pro Phe Pro Gln Pro Gln Leu Pro Tyr
1               5                   10
```

<210> SEQ ID NO 65
<211> LENGTH: 11
<212> TYPE: PRT
<213> ORGANISM: Artificial
<220> FEATURE:
<223> OTHER INFORMATION: minimal eptiope for anti-Glia-alfa2/9 mAb

<400> SEQUENCE: 65

Leu Gln Pro Phe Pro Gln Pro Gln Leu Pro Tyr
1               5                   10

<210> SEQ ID NO 66
<211> LENGTH: 11
<212> TYPE: PRT
<213> ORGANISM: Artificial
<220> FEATURE:
<223> OTHER INFORMATION: minimal eptiope for anti-Glia-alfa2/9 mAb

<400> SEQUENCE: 66

Gln Pro Phe Pro Gln Pro Gln Leu Pro Tyr Pro
1               5                   10

<210> SEQ ID NO 67
<211> LENGTH: 8
<212> TYPE: PRT
<213> ORGANISM: Artificial
<220> FEATURE:
<223> OTHER INFORMATION: minimal eptiope for anti-Glia-agamma1 mAb

<400> SEQUENCE: 67

Phe Pro Gln Gln Gln Arg Pro Phe
1               5

<210> SEQ ID NO 68
<211> LENGTH: 8
<212> TYPE: PRT
<213> ORGANISM: Artificial
<220> FEATURE:
<223> OTHER INFORMATION: minimal eptiope for anti-Glia-agamma1 mAb

<400> SEQUENCE: 68

Pro Gln Gln Gln Arg Pro Phe Ile
1               5

<210> SEQ ID NO 69
<211> LENGTH: 8
<212> TYPE: PRT
<213> ORGANISM: Artificial
<220> FEATURE:
<223> OTHER INFORMATION: minimal eptiope for anti-Glia-agamma1 mAb

<400> SEQUENCE: 69

Gln Gln Gln Arg Pro Phe Ile Gln
1               5

<210> SEQ ID NO 70
<211> LENGTH: 8
<212> TYPE: PRT
<213> ORGANISM: Artificial
<220> FEATURE:
<223> OTHER INFORMATION: minimal eptiope for anti-Glia-agamma1 mAb

<400> SEQUENCE: 70

Gln Gln Arg Pro Phe Ile Gln Pro

```
<210> SEQ ID NO 71
<211> LENGTH: 9
<212> TYPE: PRT
<213> ORGANISM: Artificial
<220> FEATURE:
<223> OTHER INFORMATION: min

```
<212> TYPE: PRT
<213> ORGANISM: Artificial
<220> FEATURE:
<223> OTHER INFORMATION: minimal eptiope for anti-LMW glutenin mAb

<400> SEQUENCE: 77

Ser Gln Gln Gln Gln Pro Pro Phe Ser Gln Gln Gln Gln Ser Pro
1               5                   10                  15

<210> SEQ ID NO 78
<211> LENGTH: 15
<212> TYPE: PRT
<213> ORGANISM: Artificial
<220> FEATURE:
<223> OTHER INFORMATION: minimal eptiope for anti-LMW glutenin mAb

<400> SEQUENCE: 78

Pro Phe Ser Gln Gln Gln Gln Pro Pro Phe Ser Gln Gln Gln Gln
1               5                   10                  15

<210> SEQ ID NO 79
<211> LENGTH: 15
<212> TYPE: PRT
<213> ORGANISM: Artificial
<220> FEATURE:
<223> OTHER INFORMATION: minimal eptiope for anti-LMW glutenin mAb

<400> SEQUENCE: 79

Phe Ser Gln Gln Gln Gln Pro Pro Phe Ser Gln Gln Gln Gln Ser
1               5                   10                  15

<210> SEQ ID NO 80
<211> LENGTH: 15
<212> TYPE: PRT
<213> ORGANISM: Artificial
<220> FEATURE:
<223> OTHER INFORMATION: peptide

<400> SEQUENCE: 80

Pro Pro Phe Ser Gln Gln Gln Gln Ser Pro Phe Ser Gln Gln Gln
1               5                   10                  15

<210> SEQ ID NO 81
<211> LENGTH: 15
<212> TYPE: PRT
<213> ORGANISM: Artificial
<220> FEATURE:
<223> OTHER INFORMATION: minimal eptiope for anti-LMW glutenin mAb

<400> SEQUENCE: 81

Pro Phe Ser Gln Gln Gln Gln Ser Pro Phe Ser Gln Gln Gln Gln
1               5                   10                  15
```

METHOD FOR DETECTING GLUTEN

This application is the U.S. National Phase of, and Applicants claim priority from, International Application Number PCT/NL2005/000400 filed 1 Jun. 2005 and European Patent Application bearing Serial No. EP 04076902.8 filed 30 Jun. 2004, which are incorporated herein by reference.

BACKGROUND OF THE INVENTION

The invention relates to the fields of immunology and Coeliac disease. The invention in particular relates to the antibodies generated against different gluten proteins involved in Coeliac disease and uses thereof for the detection of those proteins in different backgrounds as there are/ for instance; protein (digests) of wheat, food products, wheat starch hydrolysates, protein hydrolysates of wheat proteins, raw materials and semi-finished materials used in food industry.

Coeliac disease (CD) is a permanent intolerance for wheat gluten proteins, a complex mixture of storage proteins[1]. Similar (gluten-like) proteins are present in other cereals like barley, rye, oats and triticale (a hybrid of wheat and rye). Typical symptoms observed in CD patients are chronic diarrhea, malnutrition, anemia, fatigue and growth retardation. These symptoms are the result of a lesion in the small intestine characterized by (sub) total villous atrophy and increased numbers of intraepithelial lymphocytes[2].

It is now generally accepted that CD is an immune disease caused by T cells recognizing gluten derived peptides presented by HLA-DQ2 or HLA-DQ8 molecules. Such gluten-specific, CD4+, HLA-DQ2 or HLA-DQ8 restricted, T lymphocytes can be isolated from small intestinal biopsies of patients but not of controls[3,4,5,6,7]. T cell stimulatory peptides have been identified by us an others, and these originate from proline and glutamine rich regions in α-gliadin, γ-gliadin, and low (LMW) and high molecular weight (HMD) glutenins[8,9,10,11,12,13]. Modification of these peptides, due to the activity of the enzyme tTG is in the majority of cases required for, or enhances the gluten specific T cell response. tTG activity converts glutamine residues in gluten peptides into glutamic acid which facilitates gluten peptide binding to HLA-DQ2 or HLA-DQ8[14,15,16,17]. This provides an explanation for the observation that the presence of these molecules predisposes to disease development[3,18,19,6,20,21].

Omission of gluten from the diet of CD patients leads to disappearance of CD symptoms and full recovery of the small intestine. The Codex Alimentarius defines gluten free foods as those whose gluten contents are below 200 ppm (200 mg gluten/100 g of food), which is equivalent to 100 ppm of gliadins To further ensure safety for CD patients, it has been proposed to decrease this level to 20 ppm[22].

The accurate detection of gluten however, is complicated since gluten is composed of two different protein families, the LMW and HMW molecular weight glutenins and gliadins. The latter can be further subdivided into α-, γ-, and ω-gliadins. Moreover, each subgroup of the gliadins consists of a mixture of highly similar but distinct proteins (for a recent review[23]). Another complication for the detection of gluten proteins is that they can be present in the food products both as intact protein and as small protein fragments. In order to be used in gluten free food products, wheat starch with remaining low protein content is hydrolyzed chemically or enzymatically. During this process the gluten proteins are digested into small peptides and amino acids. When this hydrolysis is incomplete, protein fragments will remain with sizes that are big enough to stimulate T cells. Moreover, protein hydrolysates are widely used in the food industry including hydrolysates originating from wheat that may also contain gluten and smaller fragments thereof.

For the detection of gluten two commercially available methods are currently available, both based on a sandwich Elisa system. In one assay ω-gliadins[24] are detected, while in the other assay both α-, γ- and ω-gliadins are detected[25]. However, when used for the screening of the safety of food used by CD patients, the methods have three major disadvantages. First, the assays are not specific for detection of T cell stimulatory sequences in gluten. Secondly, the methods that are based on a sandwich Elisa are not suitable for the detection of small peptides i.e. of sizes recognizable by T cells. Thirdly, the methods do not detect Low Molecular Weight and High Molecular Weight glutenin proteins. Consequently there is an urgent need for better assays that detect those sequences in gluten, both originating from gliadin and glutenin, that stimulate gluten specific T cells in the intestine of CD patients on both intact proteins and on peptides of sizes that can be recognized by T cells.

DESCRIPTION OF THE INVENTION

In one aspect the invention therefore provides a method for detecting gluten, a gluten-like protein or a peptidic residue thereof in a sample comprising contacting said sample with an antibody that is specific for an amino acid sequence that is indicative for the presence of a T-cell epitope in gluten or a gluten-like protein or a gluten derived peptidic residue and determining whether the antibody is bound to a target peptide in said sample. A minimal T-cell epitope is typically larger than the minimal sequence that is recognized by an antibody. However, the epitope recognized by the mAb is mostly present as part of a T cell epitope. Therefore, the results obtained with the mAb assay theoretically will be an overestimation compared to the actual amount of T cell epitopes present. When the mAb assay is used for screening of food products or ingredients used for food production for CD patients, the overestimation of T cell epitopes present in the tested material will increase safety of the products. For all practical purposes the results obtained with the antibody are sufficient to assess the presence of the T-cell epitope in a sample. Thus it is sufficient that the antibody recognizes an amino acid sequence that is indicative for the presence of a T-cell epitope in gluten or gluten-like protein or gluten derived peptidic residue. This criterion is met when the binding of the antibody to its target is dependent on the presence of T-cell epitope sequences in the target. In other words, it is sufficient that the recognition site of the antibody or other binding body has overlap with the T-cell epitope in gluten or gluten-like protein. Thus when in the present invention reference is made to an epitope that is indicative for the presence of a T-cell epitope it refers to an epitope that at least partially overlaps with said T-cell epitope. When the target motif occurs more than once in gluten, there is a possibility that a sample comprising a peptidic residue of gluten is marked positive while the T-cell epitope is not present. Thus in a preferred embodiment the target motif is unique in gluten. In this case the antibody does not bind to sites in gluten that are not associated with the T-cell epitope. A gluten derived peptidic residue originates from gluten or gluten-like protein. The residue contains peptidic fragments of 6 or more amino acids. A peptidic residue also includes peptidic residue that has undergone at least a partial deamidation step such that at least one or more of the glutamine in the amino acid sequence that is indicative for the toxic T cell epitope is deamidated. A non-limiting way in which such deamidation can be achieved is by treating pepsin/trypsin digests of gluten or gluten-like protein containing samples with tissue transglutaminase as described (11). A sample contains gluten that can have a toxic component when the sample comprises at least one of the proteins α-gliadin, γ-gliadin, low molecular weight glutinin and high molecular weight glutenin. When herein reference is made to gluten, it is a reference to gluten that can have a toxic component for CD disease patients. A gluten derived peptidic derivative or residue comprises a peptidic derivative of α-gliadin, γ-gliadin, low molecular weight glutenin and high molecular weight glutenin. Using the antibodies of the invention different levels of T cell stimulatory epitopes homologous to those present in both α-, γ-gliadin, LMW glutenin and HMW glutenin could be detected in barley, wheat, rye, triticale and/or oats. Proteins containing these homologous epitopes are designated gluten-like proteins in the present invention. This result indicates that the mAb's not only detect the T cell epitopes present in gliadin, LMW glutenin and HMW glutenin but also those present in other homologous proteins like the hordeins of barley, the secalins of rye and the avenins of oats. This broad cross reactivity of the mAb is a major advantage compared to already existing gluten detection methods since the mAb used in a commercial assay for the detection of ω-gliadin only low cross reactivity was found with the hordeins and no cross-reactivity with the avenins[24]. Moreover, with an assay detecting α-, γ- and ω-gliadin no cross-reactivity with avenin was detected[25]. Thus when in the present invention reference is made to an assay for the detection of gluten or an antibody for the detection of gluten, said assay and said antibody or equivalent thereof is also capable of detecting T-cell epitopes from gluten-like homologues proteins or peptidic derivatives thereof.

In a preferred embodiment the T-cell epitope is an MHC-class II epitope presented to the T cells by HLA-DQ-2 or HLA-DQ-8, as the presence of these HLA molecules in an individual is exclusively associated with CD. The binding of the antibody is preferably determined in a competition assay. Preferably with a detectable, and preferably synthetic, competitor molecule. In a preferred embodiment a competition method of the invention comprises detecting binding of a competitor target to said antibody. The competitor can be any substance capable of specifically competing for binding to the antibody used in the assay. In a preferred embodiment the competitor comprises a T cell epitope together with flanking amino acids generally present in a gliadin or glutenin protein. In a particular preferred embodiment the competitor is a competitor of table 2 or a functional equivalent thereof. It is of course understood that the competitors of table 2 are only usable with the respective antibody. For instance, the HMW glutenin competitor is to be used in the assay with a HMW glutenin specific antibody that recognizes the competitor. A competition assay can easily be quantitated. By the use of only one antibody in a competition assay, next to intact proteins, also peptidic residues of gluten may be analyzed for the presence of the mentioned T-cell epitopes. Preferably, the competitor is labeled.

The above-mentioned method and other methods of the invention for the detection of the presence of known T cell stimulatory peptides originating from gluten have a very low detection limit Relating to the assays for α-, γ-gliadin, LMW glutenin and HMW glutenin and using the European gliadin reference IRMM-480[2G] or synthetic peptides encoding the T cell epitope detected by the mAb, a method of the invention can reach a detection limit that allows the detection of gluten in food extracts below the new threshold of 20 ppm proposed by the Codex Alimentarius[22].

It is possible to use any antibody having the mentioned specificity for T-cell epitopes, however, in a preferred embodiment an antibody or a functional part, derivative and/or analogue thereof of the invention is used, preferably having a sequence as depicted in Table 3. These antibodies have a unique specificity that makes them particularly suitable for the present invention. A method of the invention preferably comprises at least two and preferably at least three antibodies comprising a sequence as depicted in table 3 or a functional part, derivative and/or analogue thereof. More preferably, a method of the invention comprises at least four antibodies comprising a sequence as depicted in table 3. A method of the invention is preferably performed in a quantitative way. It is preferred that in a competition test of the invention, a labelled competitor peptide is measured or detected. Although in principle any substance or peptide capable of competitively binding to the antibody in the assay can be used, it is preferred that the competitor comprises a peptide of table 2. Such a peptide comprises an exact copy of the binding site of an antibody of the invention and therefore is a good competitor for the binding of similar peptides in the sample. It is preferred that the competitor is labelled. The method may be performed in any setting, however, ELISA or dipstick settings are preferred.

The sample is preferably a food stuff, preferably ready for consumption. These types of sample allow for safety screening of (components) of meals which can subsequently be qualified as safe or not safe for consumption by CD patients. In another embodiment the food stuff is an intermediate product for a ready to consume food stuff. Many different additives or raw materials comprise material that is derived from a source of gluten. Such additives and raw materials may be screened for the presence of gluten and thereby allow for making an informed decision on the inclusion thereof in a food stuff. The sample may also comprise a hydrolysate of a cereal or food stuff. In yet another embodiment the sample comprises teff or a component thereof. As used herein a cereal is defined as a cereal grain such as wheat, oats, maize, rice, barley, buckwheat and other starchy grains which are typically used as food.

At present many gluten-derived T cell stimulatory peptides are known and they originate from the α- and γ-gliadins, and the HMW- and LMW-glutenin. Homologues (i.e. gluten-like) sequences thereof are, for example, found in the secalins of rye, the hordeins of barley and the avenins of oats. Gluten and gluten-like proteins thus contain many immunogenic peptides. Moreover, the unique food-industrial properties of gluten are in part related to a very high praline content which renders gluten relatively resistant to enzymatic degradation in the gastrointestinal tract (45-47). Hence, many of the immunogenic gluten peptides are likely to survive for extended periods in the intestine, increasing the probability of triggering a T cell response. Thus, the unique properties of gluten are tightly linked to their disease-inducing potential in CD patients. Each wheat plant contains a few (HMW) to several hundred (alpha-gliadins) copies of gliadin and glutenin genes (48), but it is unknown whether all these genes encode proteins that are equally harmful for patients. The first indication that heterogeneity may exist in this respect came from our observation that not all α-gliadins contained equal copy numbers of a particular T cell stimulatory peptide (44). Moreover, the genus Triticum harbors several species, of which Triticum aestivum is the most widely used in the food industry. Thousands of Triticum accessions are available in genebanks. The oldest material is diploid and contains the AA, BB/SS, or DD genome. These grass-like species have a very low seed yield and drop their seed easily. Due to natural hybridization between some of these species the tetraploid Triticum species with the AABB genotype (pasta wheat) originated. Finally, through spontaneous hybridization between tetraploid and diploid species around 4000 BC, hexaploid wheat (AABBDD) species were formed. Further breeding during the last centuries led to an increase in gluten content, enhanced crop yield and other properties that are important for the application of hexaploid bread wheat in food production. The existence of thousands of different Triticum accessions raised the question whether all Triticum accessions are equally toxic for CD patients. Recently, two assays have become available that for the first time allow a rational screening of wheat and food products for the presence of T cell stimulatory gluten sequences. In the first assay, gluten-specific T cell clones that have been isolated from intestinal biopsies of CD patients are used. In the second assay, monoclonal antibodies specific for T cell stimulatory gluten peptides are used (49 and the present invention).

In the present invention we show that there are considerable differences in the levels of T cell stimulatory epitopes among cereals. Together with the observation that individual gluten molecules contain highly variable numbers of T cell stimulatory sequences, these results allow, through rational screening and breeding strategies, the identification and/or selection of cereal varieties with a reduced or even absent toxicity profile for CD patients. Such varieties contribute to improved and safe diet that contains material from plant species with gluten or glutin-like proteins, for CD patients. In one aspect of the invention, the method is used to screen plants for the presence therein of gluten or similar components Plants that are (made) essentially free of toxic epitopes may be selected for breeding. Such plants can be used to produce specific toxic epitope free plants or plants that have a low content of said particular toxic epitope. As the genetic make up of a stable breed of plants does not change upon breeding it is possible to produce plant lines that do not comprise the specific toxic epitopes. Thus in one embodiment a method of the invention further comprises multiplying the plant or an equivalent thereof when a T-cell epitope in gluten or gluten-like protein or a gluten derived peptidic residue was low or not detected in said sample.

Now that the present invention provides antibodies or functional parts, derivatives and/or analogues thereof that can be used to determine whether gluten or gluten-like protein producing cereals produce toxic epitopes, the present invention provides the use of one or more of these antibodies or equivalents thereof for screening purposes. In the present invention it has been found that cereals comprise a considerable genetic diversity, already at the genus level. This diversity allows for the selection of species, strains and/or variants that comprise a low amount or a not detectable amount of the amino acid sequence that is indicative for the presence of a T-cell epitope in gluten or gluten-like protein that the antibody is specific for. Thus the invention further provides the use of at least one antibody or functional part, derivative and/or analogue thereof, that is specific for an amino acid sequence that is indicative for the presence of a T-cell epitope in gluten or gluten-like protein or a gluten derived peptidic residue thereof, for selecting a cereal. The selected cereal preferably produces a low amount or a not detectable amount of said amino acid sequence. In a preferred embodiment said antibody or functional part, derivative and/or analogue thereof is used for selecting a cereal for food production. Preferably wherein food or precursors thereof produced with said cereal exhibit low or absent binding to said at least one antibody of the invention or a functional part, derivative and/or analogue thereof.

Any antibody or functional part, derivative and/or analogue thereof having the mentioned specificity can be used in the present invention. However, in a preferred embodiment said antibody is an antibody of table 3, or a functional part, derivative and/or analogue thereof. An antibody of table 3 preferably comprises both a heavy and a light chain of anti-α-gliadin, anti-γ-gliadin, anti-LMW-glutenin (1), anti-LMW-glutenin (2) or anti HMW-glutenin depicted in table 3. Thus in a preferred embodiment said at least one antibody is specific for an α-gliadin, a γ-gliadin, a LMW glutenin or a HMW-glutenin comprising said amino acid sequence indicative for a (toxic) T cell epitope. A cereal having a low or undetectable amount of one amino acid sequence that is indicative for the presence of a T-cell epitope in gluten or gluten-like protein or a gluten derived peptidic residue thereof, is already useful in the production of food or a food precursor for Coeliac patients. Further reduction of toxic epitopes can be accomplished by methods in the art such as, but not limited to proteolytic cleavage.

Using a cereal selected in the invention at least reduces the amount toxic epitopes in the starting material. In a preferred embodiment, at least two of said antibodies are used for selecting said cereal. Said at least two antibodies are, preferably, specific for different gluten, gluten-like protein or a gluten derived peptidic residue thereof or a functional part, derivative and/or analogue thereof. In a particularly preferred embodiment at least four of said antibodies are used for selecting said cereal and wherein said at least four antibodies are specific for a different gluten, gluten-like protein or a gluten derived peptidic residue thereof or a functional part, derivative and/or analogue of thereof. In a preferred embodiment, said at least two and or at least four antibodies are antibodies depicted in table 3, or functional parts, derivatives and/or analogues thereof. Preferably a first of said antibodies is specific for an α-gliadin, a second of said antibodies is specific for a γ-gliadin, a third of said antibodies is specific for a LMW glutenin and a fourth is specific for a HMW-glutenin. In a preferred embodiment a use of the invention is for selecting a cereal for food production and wherein food or precursors thereof produced with said cereal exhibit low or absent binding to said at least two antibodies or functional parts, derivatives and/or analogues thereof. Preferably for selecting a cereal for food production and wherein food or precursors thereof produced with said cereal exhibit low or absent binding to said at least four antibodies or functional parts, derivatives and/or analogues thereof.

The invention further provides a method for selecting a cereal from a collection of cereals comprising determining binding of a gluten specific antibody according to table 3 to gluten-containing (seed.) samples of said collection of cereals and selecting from said collection a cereal that produces gluten that exhibits less binding of said antibody. Cereal seeds are used for many different purposes. As seeds typically contain gluten, many of these purposes are adapted for using seeds that contain at least a certain amount of gluten. Methods for detecting one or more amino acid sequences that are indicative for the presence of a T-cell epitope in gluten or gluten-like protein or a gluten derived peptidic residue thereof, can be used as an indicator for the presence or absence of said amino acid sequence. However, in another setting methods of the invention can be used to estimate the presence or absence of intact or 'partially' degraded gluten or gluten-like protein in a sample such as but not limited to food, food derivative and/or food precursor. This embodiment is for instance useful for monitoring gluten removal and/or degradation processes. These processes are currently carried out to prepare food or food precursors for Coeliac patients. Such processes can, in the present invention be monitored with one or more antibodies of the present invention, and/or with functional parts, derivatives and/or analogues thereof. The antibodies of the present invention are particularly suited for this purpose as they are specific for amino acid sequences that are indicative for the presence of a T-cell epitope in the four different gluten, gluten-like proteins or derived peptidic residue thereof. Thus removal, and/or degradation can be followed for the different gluten or gluten-like proteins, which behave differently in the various clearing methods. The antibodies or functional parts, derivatives and/or analogues thereof have the additional advantage that they are specific for amino acid sequences that are indicative for the presence of T-cell epitopes in gluten or a gluten derived peptidic residue thereof. The resulting information is thus not only indicative for the amount of removal and/or degradation of gluten or gluten-like proteins, but in addition a direct indication for the removal and/or degradation of one or more toxic epitopes, depending on the number of different antibodies used.

Monitoring removal of gluten or gluten-like proteins can also used for selecting a cereal that has at least a reduced amount of gluten or gluten-like protein. This is, for instance, useful in cereal mutation programs. By screening seeds of said mutants with a method of the invention it is possible to select mutants that produce no or a low amount of the particular gluten or gluten-like protein. Alternatively when a collection of natural or mutant cereals is screened it is possible to select a natural or mutant cereal that has no or a low amount of the particular gluten or gluten-like protein. The selected cereal can be used directly for the production of a food or a precursor thereof. Alternatively, the cereal is entered into a cross-breeding program and a method of the invention is used to select progeny that has both the genetic information for the low or absent amount of gluten or gluten-like protein and one or more favourable characteristics of the other parent strain(s). In yet another embodiment, the gene encoding the gluten and/or gluten-like protein in the selected cereal is cloned and introduced into a different cereal. Thus the present invention also provides using the gene encoding the gluten or gluten-like protein that said antibody is in general specific for or a functional part, derivative and/or analogue of said gene, for producing a modified cereal that produces gluten or gluten-like protein that exhibits no or less binding of said antibody. A functional part of said gene comprises at least a nucleic acid sequence of said gene encoding the amino acid sequence that is present at the site where in a reference gluten or gluten-like protein said toxic T-cell epitope is located. A derivative of said gene comprises a nucleic acid sequence encoding an amino acid sequence that is derived from the site in said gene where in a reference gluten or gluten-like protein said toxic T-cell epitope is located but that is different in at least one amino acid. The derivative is of course also different in at least one and preferably at least two amino acids from said toxic T cell epitope. An analogue of said gene is a gene derived from a different cereal that comprises at least one different and preferably at least two different amino acids from said toxic T cell epitope at the site where in a reference gluten or gluten-like protein said toxic T-cell epitope is located.

A method of this embodiment preferably further comprises producing a food or a precursor therefore from said selected cereal.

A sample that is analysed with a method of the invention is preferably a sample that would normally be expected to contain gluten or a gluten-like protein. Thus when in the present invention reference is made to a sample of a cereal, said sample preferably comprises protein obtained from seed of said cereal. Thus the invention also provides a method for determining genetic variation in a collection of cereals comprising determining binding of at least one gluten specific binding body with gluten containing seed samples of said collection, wherein said gluten specific binding body is specific for an amino acid sequence that is indicative for the presence of a T-cell epitope in gluten or gluten-like protein or a peptidic residue thereof. There are many different binding bodies in the art. A binding body of the invention can be any binding body capable of binding an amino acid sequence or a peptidic derivative thereof. Of these binding bodies the antibodies, or functional parts, derivatives and/or analogues thereof are preferred.

A method for selecting a cereal from a collection of cereals preferably further comprises determining binding of at least two gluten specific binding bodies with gluten or gluten-like protein containing seed samples of said collection, wherein said at least two gluten specific binding bodies are specific for an amino acid sequence that is indicative for the presence of a T-cell epitope in gluten or gluten-like protein or a peptidic residue thereof. In a preferred embodiment said method further comprises determining binding of at least four gluten specific binding bodies that are specific for an amino acid sequence that is indicative for the presence of a T-cell epitope in gluten or gluten-like protein or a peptidic residue thereof, in gluten containing seed samples from said collection. A first of said binding bodies is preferably specific for one gluten or peptidic residue thereof, and a second of said antibodies is preferably specific for a different gluten or peptidic residue thereof. For reasons mentioned earlier it is preferred that a third and a fourth of said binding bodies are specific for yet further different gluten or peptidic residue thereof. A method of the invention for selecting a cereal preferably further comprises selecting a variety/species that produces at least one gluten or gluten-like protein that exhibits a low or absent binding to said at least one binding body. Preferably, said method further comprises selecting a variety/species that produces at least one gluten or gluten-like protein that exhibits a low or absent binding to at least said second binding body. In this way at least two cereals are selected wherein one cereal has a low or absent amount of one gluten or gluten-like protein and at least one other cereal has a low or absent amount of another gluten or gluten-like protein. In a preferred embodiment of the invention, said at least two cereals are entered into a cross-breeding program. The method therefore preferably comprises producing a cereal that combines the genetic information responsible for said low or absent binding to said first binding body with the genetic information responsible for said low binding or absent binding to said second binding body. Preferably, said method further comprises producing a cereal that further combines the genetic information responsible for said low or absent binding to said third binding body and the genetic information responsible for said low or absent binding to said fourth binding body. The produced cereals may further be cross-bred with other strains to include other toxic epitope related properties in further progeny. As mentioned above, it is preferred that at least one of said binding bodies is an antibody depicted in table 3, or a functional part, derivative and/or analogue thereof. Preferably, at least four of said binding bodies are antibodies depicted in table 3 or functional parts, derivatives and/or analogues thereof. In a particularly preferred embodiment said cereal comprises a cereal of the genus *Triticum.*

The invention further provides a modified cereal obtainable by a method of the invention. Preferably said cereal comprises the genetic information responsible for said low or absent binding to said first binding body and the genetic information responsible for said low binding or absent binding to said second binding body. Preferably said cereal further comprises the genetic information responsible for said low or absent binding to said third binding body. More preferably, said cereal further comprises the genetic information responsible for said low binding or absent binding to said fourth binding body. In yet another embodiment the invention provides a modified cereal of the invention wherein said cereal is of the genus *Triticum*.

Methods and uses of the invention are suited for the selection of (mutant) cereals having no detectable amount of an amino acid sequence that is indicative for the presence of a T-cell epitope in gluten or gluten-like protein or a gluten derived peptidic residue thereof. A low amount of said amino acid sequence in the present invention means that a binding body or an antibody of the invention or a functional part, derivative and/or analogue thereof detects an amount that is less than 20% and preferably less than 10 and preferably less than 5% and even more preferred less than 2% of the amount detected in cereal *Triticum turgidum* group cathlicum CGN 08360 (Table 6 and 8).

The invention provides an antibody (I) specific for a peptide with an amino acid sequence QLQPFPQPQLPYPQP (SEQ ID NO: 1). This sequence comprises a T-cell epitope that is present in [alpha]-gliadin. In a preferred embodiment the antibody is specific for a peptide with an amino acid sequence XQPFPQPQLPYP (SEQ ID NO: 2) and more preferably for the motif XQPFPQPQ (SEQ ID NO: 3) therein. The X in the latter two sequences indicates that for recognition of the epitope there is a need for an amino acid at the position of X but that the type of amino acid does not matter. In another embodiment the invention provides an antibody specific for a peptide with an amino acid sequence QPQQPQQSFPQQQRPFIQPSLQ (SEQ ID NO: 4). Preferably the antibody (II) is specific for a peptide with an amino acid sequence QQRPFI (SEQ ID NO: 5). In yet another embodiment the antibody is specific for a peptide with an amino acid sequence QPPFSQQQQSPFSQ (SEQ ID NO: 6). Preferably the antibody (III) is specific for a peptide with an amino acid sequence PPFSQQ (SEQ ID NO: 7). In yet another embodiment the antibody (IV) is specific for a peptide with an amino acid sequence QPPFSQQQQSPFSQ (SEQ ID NO: 6). Preferably the antibody is specific for a peptide with an amino acid sequence QSPFS (SEQ ID NO: 8). The invention further provides an antibody (V) specific for a peptide with an amino acid sequence PGQGQQGYYPTSLQQP (SEQ ID NO: 9), PGQGQQGYYPTSQQQP (SEQ ID NO: 10), PGQGQPGYYPTSLQQP (SEQ ID NO: 11), PGQGQPGYYPTSQQQP (SEQ ID NO: 12), QGQQGYYPTSPQQP (SEQ ID NO: 13) or QGQQGYYPTSPQQS (SEQ ID NO: 14). Preferably said antibody (V) is specific for all of the mentioned epitopes. The antibodies or functional parts, derivatives and/or analogues thereof, mentioned in this paragraph also recognize deamidated versions of the mentioned peptides.

The invention further provides an antibody or a functional part, derivative and/or analogue of an antibody having a sequence as depicted in table 3. A functional derivative comprises at least one of the CDR3 sequences of the heavy and/or light chain of anti-α-gliadin, anti-γ-gliadin, anti-LMW-glutenin (1), anti-LMW-glutenin (2) or anti HMW-glutenin depicted in table 3. Preferably, said derivative comprises both CDR3 sequences. Antibodies have been intensively investigated over the years. Antibodies may be modified in various ways. For instance, various techniques have been devised to graft CDR sequences from one antibody to the other thereby providing the receiving antibody with at least part of the binding specificities of the donor antibody. Thus a CDR sequence and preferably a CDR3 sequence of an antibody of the invention may be grafted onto another antibody thereby providing the receiving antibody with at least part of the target binding characteristics of the antibody of the invention. This technique is for instance used to humanize an antibody derived from a non-human animal Such derivatives are also art of the invention and can be used as method of the invention.

In a preferred embodiment the antibody comprises all CDR sequences of a mAb depicted in table 3. In this case the binding specificity and affinity of the original antibody are at least approximated. Grafting CDR sequences onto another antibody can be done in various ways. It can be done by only transplanting the particular one or more CDR sequences. It can however, also be done by simultaneously grafting the framework regions, or a large part of the variable region(s) onto the receiving antibody. Typically, but not necessarily, the grafting is done through exact replacement of a part of the receiving antibody by the corresponding inserted sequences. Such derivatives are also part of the invention and can be used in a method of the invention. In a particular preferred embodiment the antibody comprises the variable sequences of a mAb of table 3. Other alterations are also possible. For instance, derivatives can be made through replacement, deletion or insertion of amino acids in regions that are generally known as to be not essential for binding of the antibody to the target site. Or by replacing essential amino acids for amino acids that are known to function in an equivalent fashion. For instance, framework regions of antibodies are known to provide structural context for the CDR regions. There are many different framework regions that can provide this structural context and such chimearic antibodies are therefore also part of the invention.

The antibody can be generated in any type of non-human animal. The antibody can also be derived from a human that was immunized with a peptide of the invention, or from an immunized transgenic animal comprising a human antibody locus. The antibody can thus be from any animal, but is typically derived from an animal normally used for such purposes such as mouse, rat, rabbit, llama and camel.

An antibody of the invention can also be specific for a derivative of a peptide mentioned above. At least some chemical or enzymatic modification of the peptide is typically though not necessarily tolerated without essentially affecting the binding efficiency of the peptide to the antibody.

Now that the present invention provides antibodies having the above-mentioned characteristics it is easily possible to generate parts or analogs of antibodies of the invention. Such parts or analogues binding bodies have similar binding characteristics in kind, not necessarily in amount, and are also provided for by the invention. For instance, it is typically sufficient to retain the binding specificity using fragments of antibodies that retain at least the CDR region of the antibody. Non-limiting examples of such fragments (parts) are single chain Fv fragment, FAB fragments, monobodies and the like. It is for instance possible to generate antibodies having only the equivalent of a heavy chain of a 'normal' antibody, for instance llama and camel antibodies. Such 'heavy chain only' antibodies compensate the loss of specificity through lack of light chain CDR regions by having particular CDR structures in the heavy chain. Now that the invention provides the methods for using antibodies having the particular specificity for the peptides of the invention it is clear that such antibodies are analogs that are also included in the present invention. Also non-antibody binding bodies are analogs that are included in the present invention. Using, for instance, phage display techniques, it is possible to generate binding bodies having any particular specificity. Thus the invention provides any proteinaceous binding body having a binding specificity for an amino acid sequence that is indicative for the presence of a T-cell epitope in gluten or gluten-like protein or gluten derived peptidic residue. Such binding body may be used in any of the methods or uses of the present invention.

The invention further provides a peptide comprising a CDR sequences as depicted in table 3. Further provided is a nucleic acid encoding a CDR sequence as depicted in table 3. Also provided is a cell comprising such a peptide and/or nucleic acid.

In another aspect the invention provides the use of an antibody of the invention to determine whether a sample comprises a target for said antibody. Preferably the antibody is used in a quantitative assay. The invention further provides the use of an antibody of the invention for the detection of gluten proteins or peptidic derivatives thereof in food samples, and thereby for suitability for ingestion by individuals suffering from Coeliac Disease or at risk of suffering there from. Provided is also the use of an antibody of the invention for the detection of gluten proteins or peptidic derivatives thereof in basic or semi manufactured ingredients used in food industry. Provided is also the use of an antibody of the invention for the detection of gluten proteins or proteins homologous to gluten or peptidic derivatives thereof present in different cereals. Preferably the gluten proteins are intact or partially degraded (i.e. a peptidic derivative of gluten). Preferably the antibody is used for the detection of T cell stimulatory sequences in a sample (suspected of) comprising gluten.

The invention further provides a method for detecting known T cell stimulatory peptides originating from α-gliadin, γ-gliadin, low molecular weight glutenin and/or high molecular weight glutenin or homologous (glutenin-like proteins) in intact proteins and/or peptidic derivatives thereof in a sample comprising generating an antibody specific for an amino acid sequence indicative for the presence of at least one of said T cell stimulatory peptides and determining whether said antibody specifically binds to a peptide or a derivative thereof in said sample. In a preferred embodiment the antibody is an antibody of the invention. More preferably an antibody specific for a T-cell epitope of table 1. In yet another preferred embodiment a method for detecting a T-cell epitope or stimulatory peptide originating from gluten comprises detecting at least two and preferably at least three different peptides or derivatives thereof.

The antibodies provided in the present invention have been raised against a synthetic peptide comprising a T cell epitope QPFPQPQLPYPQP (SEQ ID NO: 15), PQQSFPQQQR-PFIQPSL (SEQ ID NO: 16), PPFSQQQQSPFS (SEQ ID NO: 17), PGQGQ(Q/P)GYYPTS(L/Q)QQP (SEQ ID NO: 18) or QGQQGYYPTSPQQ(P/S) (SEQ ID NO: 19), wherein the latter two epitopes exhibit divergence indicated by the alternative amino acid depicted in brackets. The invention therefore provides a tagged/labeled peptide having said sequence, preferably together with natural occurring adjacent amino acids so that the T cell stimulatory epitope is placed in its natural context, which is suitable for quantification of the gluten proteins detected by the antibodies of the invention. The invention further provides a conjugate comprising said peptide and wherein said peptide is outside its natural context. The invention further provides said conjugate as a fusion protein.

The peptide or conjugate can be used as positive control in a method for detecting a T-cell epitope of the invention. The preferably labeled peptide or conjugate can be used as a competitor in a competition assay of the invention. Thus the invention further provides the use of said peptide or conjugate for the detection of an antibody of the invention. In another aspect is provided the use of said peptide or conjugate according for immunizing a non-human animal.

The invention is further explained in the experimental part of this description without limiting the invention thereto.

EXAMPLES

Example 1

Materials and Methods

Synthetic Peptides

Peptides were synthesized by standard Fmoc chemistry on a SyroII peptide synthesizer. The integrity of the peptides was checked by rpHPLC and mass spectrometry. The S-acetyl-mercaptoacetic acid (SAMA) group was introduced in the resin-bound peptides by coupling of a 6-fold equimolar mixture of S-acetyl mercaptoacetic acid N-hydroxysuccinimide ester and 1-hydroxybenzotriazole in NMP during two hours. Biotin was introduced in the resin-bound peptides by a two hour coupling with a 6-fold equimolar preactivating mixture of biotin and PyBop/NMM.

Chemical Cross-Linking of Synthetic Peptides to Tetanus Toxoid (TTd) or Bovine Serum Albumin (BSA)

For crosslinking to TTd or BSA, an N-terminal S-acetyl-mercaptoacetic acid group (SAMA) was coupled to the peptides. The carrier proteins TTd and BSA (12 mg) were desalted and equilibrated in 1.8 ml of 100 mM $NaH_2PO_4/Na_2HPO_4$ pH 7.8. In the carrier proteins bromoacetyl groups were introduced by adding 50 µl of a solution of 23.6 mg/ml succinimidylbromoacetate in 100 mM N, N-dimethylacetamide. After 1 hour the reaction mixture was desalted and equilibrated in 3 ml 100 mM $NaH_2PO_4/Na_2HPO_4$, 5 mM EDTA pH 6.0. The SAMA-peptides (5 mg) were solubilized using 50 µl of 10% SDS and diluted in 200 µl 100 mM $NaH_2PO_4/Na_2HPO_4$, 5 mM EDTA pH 6.0. To the peptide solution 2 ml of the bromo-acetylated carrier protein mixture was added together with 25 µl 2 M hydroxylamine. After 24 hours at room temperature the reaction was stopped by adding 150 µl of 38 mM 2-aminoethanethiol. Finally the reaction mixture was desalted and equilibrated in 3.3 ml 10 mM $NaH_2PO_4/Na_2HPO_4$, 150 mM NaCl pH7.4.

Production and Purification and Sequencing of the of mAb Against T Cell Stimulatory Epitopes in Gluten Proteins.

BALB/c mice were immunized intraperitoneally with 150 µg of peptides chemically crosslinked to Tetanus toxoid (Table 1) suspended in Complete Freund adjuvant (CFA, Sigma-Aldrich, Zwijndrecht, The Netherlands). This was followed by three subsequent injections of 150 µg of the protein suspended in incomplete Freund adjuvant (IFA, Sigma-Aldrich, the Netherlands) at 4-wk intervals. Fusion of the spleen and lymph node cells with mouse myeloma Ag8 cells was performed according to standard procedures[27]. Culture supernatant from the resulting hybridomas was screened for the presence of anti-peptide mAb using the peptide chemically crosslinked to BSA with a different linker (Table 1). The supernatant of selected Ab producing hybridoma's was concentrated by Hemoflow dialysis units (Fresenius Medical Care, Nieuwkuijk, the Netherlands). Thereafter, mAb were purified by protein G affinity chromatography (Pharmacia Fine Chemicals, Uppsala, Sweden) according to the instructions of the manufacturer. Subclasses of mAb were determined by an isotyping dipstick method (HyCult biotechnology by, Uden, the Netherlands). Except for the anti-LMW glutenin (1) mAb which was of the IgG 3 κ subclass the mAb were of the IgG1 κ subclass. The variable regions of both the heavy and light chains of the mAb were sequenced according to the method commercialized by Novagen. (Novagen, EMB Biosciences, Inc, San Diego, United States)

ELISA for the Screening of mAb Producing Hybridomas

Peptides cross-linked to BSA (Table 1) were incubated at a concentration of 2 µg/ml in 0.1 M sodium carbonate/bicarbonate buffer, pH 9.6, for 16 h at 4° C. in microliter plates (Nunc Maxisorb Immunoplate, Nunc, Copenhagen, Denmark) (100 µl/well). The plates were then washed with PBS/0.02% (w/v) Tween-20. An identical washing procedure was performed after each incubation step, which consisted of 100 µl, except for the blocking step (150 µl). After coating, residual binding sites were blocked by 30 minutes (rain) incubation with PBS/1% Skim milk (Fluka, Zwijndrecht, the Netherlands). Supernatant of the hybridoma's was 1:100 diluted in PBS/0.1% Tween-20 and incubated for 1 hr. Next the plates were incubated with an excess of biotinylated rabbit-anti-mouse antiserum for 1 followed by an 30 min incubation with streptavidin-polymerized horseradish peroxidase (CLB, Amsterdam, The Netherlands). Bound peroxidase was visualized by incubation with a solution of 3,3',5,5'-tetramethylbenzidine (Sigma-Aldrich, Zwijndrecht, The Netherlands). Finally, the absorbance at 620 nm was read on a Multiscan plate reader (Wallas, Turku, Finland).

Competition Assays for the Quantitative Detection of T Cell Stimulatory Epitopes of Gluten Proteins Microliter plates (Nunc, Copenhagen, Denmark) were incubated overnight with 2-5 µg/ml mAb in 0.1 M sodium carbonate/bicarbonate buffer pH 9.2 at room temperature (RT). Plates were washed in PBS/0.02% Tween-20 and residual binding sites were blocked with PBS 1% Skim milk powder (Fluka, the Netherlands). Of the gluten containing samples different dilutions were made in PBS/0.1% Tween-20/0.1% Skim milk and these were mixed with either a biotinylated α-, γ-gliadin or LMW glutenin T cell epitope encoding peptides (Table 2). For quantification a standard curve was made by the European gliadin reference IRMM-480[26] in a concentration range of 100 µg/ml-3 ng/ml that was mixed with the biotinylated indicator peptides. The mixtures were incubated on the plates for 1.5 h at RT. Next plates were washed and incubated for 30 min with streptavidin conjugated horseradish peroxidase in PBS/0.1% Skim milk, hereafter bound peroxidase was visualized as described.

Commercial Gluten Detection Hit

The gluten specific Elisa was performed according to the instructions of the manufacturer[28].

Gliadin Standard

The new European gluten reference[26] IRMM-480 was used as a standard. The standard was dissolved in 40% aqueous ethanol and stored at 4° C.

Preparation and Measurement of Gluten Containing Starch and Food Samples

For the measurement of the gluten content of starch and food samples, 1 g of the material was incubated with 10 ml of 40% ethanol to extract the gluten. After addition of the ethanol the samples were incubated for 1 h at room temperature in a rotary shaker with recurrent vortexing for 30 seconds. Subsequently the samples were centrifuged for 2500 g for 10 min at room temperature and supernatants were transferred to eppendorf tubes. Extraction and analysis were performed on the same day.

Preparation of Gluten Containing Samples from Different Cereals

Samples of different cereals, barley, oat, wheat, rye and triticale (hybrid between wheat and rye) were grinded and a trypsin/pepsin digest was prepared as described[11]. A control sample was prepared from a commercial gliadin preparation (Fluka Chemie, Zwijndrecht, the Netherlands) using the same protocol.

T Cell Proliferation Assays

To test for the presence of T cell stimulatory epitopes in different wheat varieties two different T cell clones (one recognizing both the Glia-α2 and -9 T cell epitopes and one recognizing the Glia-α1 T cell epitope) were used. The clones originate from gluten-specific T cell lines generated from small intestinal biopsies of two different coeliac disease patients.

Proliferation assays were performed in triplicate in 150 µl Iscove's Modified Dulbecco's Medium (Bio Whittaker, Verviers, Belgium) with 10% pooled normal human serum in 96 well flat-bottom plates using $10^4$ gluten specific T cells stimulated with $10^5$ irradiated HLA-DQ2-matched allogeneic peripheral blood mononuclear cells (3000 rad) in the presence or absence of antigen (1-10 µg/ml). After 2 days $^3$H-thymidine (1 µCi/well) was added to the cultures, and 18-20 hours thereafter cells were harvested. $^3$H-thymidine incorporation in the T cell DNA was counted on a liquid scintillation counter (1205 Betaplate Liquid Scintillation Counter, LKB Instruments, Gaithersburg, Md.).

Results

Competition Assay for the Detection of T Cell Stimulatory Epitopes in Gluten.

Figure 2:
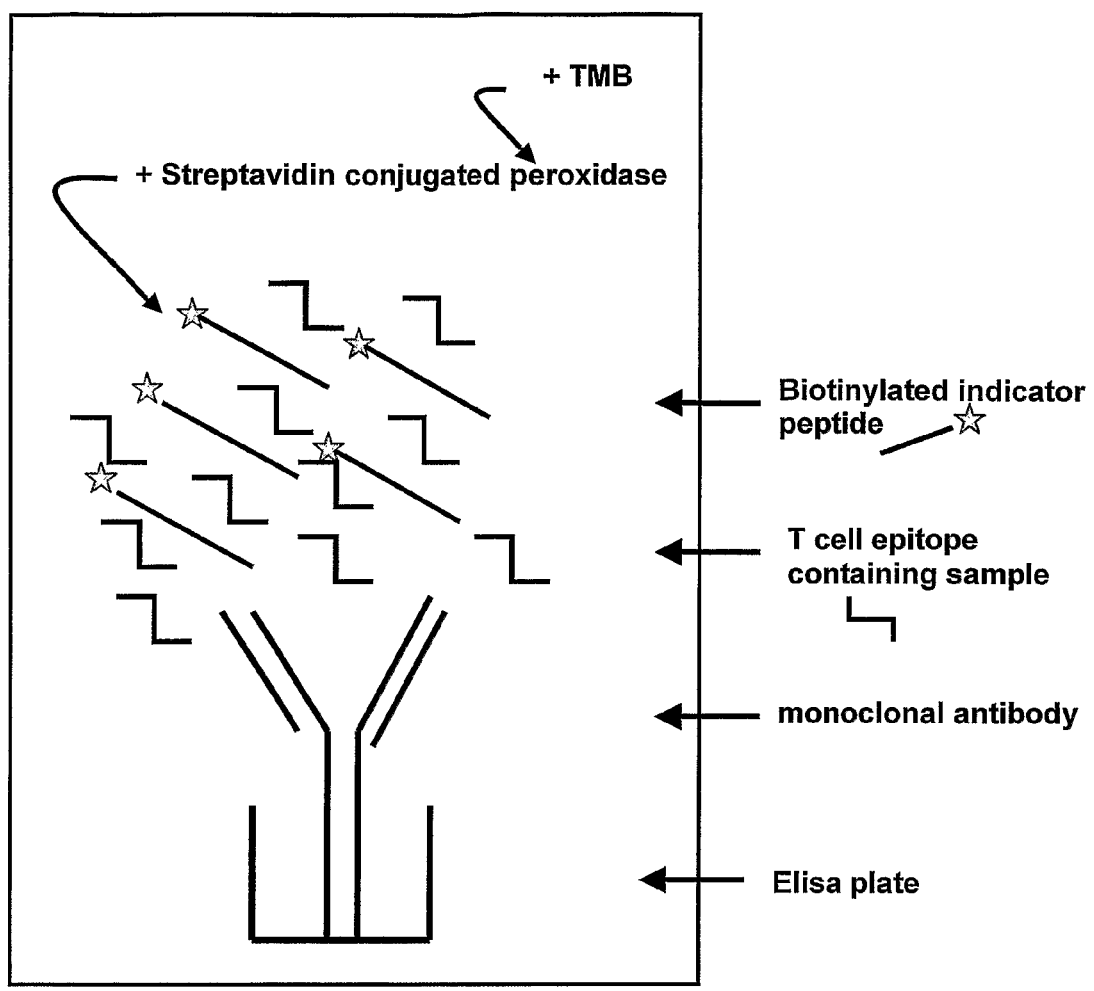

BALB/c mice were immunized with TTd coupled peptides encoding either a T cell stimulatory peptide present in α-gliadin, γ-gliadin or LMW glutenin. The spleens of the immunized mice were fused to a myeloma cell line to generate antibody secreting hybridoma cells. In this way, for both T cell stimulatory peptides several specific mAb were obtained (FIG. 1). The mAb were used to develop a competition assay. In this competition assay, the sample is mixed with a fixed concentration of a biotinylated synthetic 20-mer indicator peptide encoding the T cell epitope of either α-, γ-gliadin or LMW-glutenin. When added to an immobilized mAb, the T cell epitopes present in the sample will compete with the T cell epitopes encoded in the biotinylated indicator peptide for binding to the mAb. Depending on the gluten content of the sample more or less biotinylated indicator peptide will bind to the mAb which can be visualized with peroxidase conjugated streptavidin and TMB (FIG. 2). For each of the antigen mAb that were selected that proved the most sensitive in the competition assays. For this mAb were coated to an Elisa plate and tested for binding of the biotinylated indicator peptide (FIG. 3A). The mAb that bound to this peptide with high affinity and specificity (a titration curve upon decreasing concentrations of the biotinylated indicator peptide), were tested for their function in a competition assay (FIG. 3B). For the α-gliadin T cell epitope of the 77 mAb that were generated against the Glia-α2/9 T cell epitope only one mAb was selected that functioned in the competition assay with a sensitivity suitable for detection of T cell epitopes in various backgrounds. This mAb was obtained after immunization with peptides encoding amino acids 59-69 of α-gliadin. This mAb is referred to as anti-Glia-α2/9 hereafter. For the γ-gliadin T cell epitope of the 66 mAb specific for the Glia-γ1 T cell epitope, only one mAb was selected that functioned in a competition assay with a high enough specificity and sensitivity to be used for quantitative experiments (Result not shown). This selected mAb was obtained after immunization with amino acids 147-159 of γ-gliadin. This mAb is referred to as anti-Glia-γ1 hereafter. For LMW-glutenin of the 38 mAb specific for the Glt-156 epitope, three antibodies were selected that functioned in a competition assay with a high enough sensitivity (Result not shown). However since two of these mAb had the same specificity (see below), for quantitative experiments the mAb with different specificity were selected for the quantitative experiments. The two selected mAb are referred to as anti-LMW-glutenin1 and anti-LMW-glutenin-2 hereafter. The selected mAb were obtained after immunization with amino acids 51-58 of LMW-glutenin. For the assays the detection limit was determined using the European gliadin reference (IRMM-480)[26] as a standard. In this way sensitive assays were developed in which the gliadin reference (also containing LMW-glutenin) can be detected at a range of 100 ug/ml-12 ng/ml for both the Glia-α2/9 T cell epitope and the Glia-γ1 T cell epitope (FIG. 4). In the competition assay detecting LMW-glutenin the gliadin reference can be detected at a range of 100 ug/ml down to 24 or sometimes even 12 ng/ml (result not shown). The detection limit of 12 ng/ml is routinely reached in the competition assays for gliadin performed in our laboratory (results not shown). As a consequence, with the generally accepted method of food analysis for the presence of gliadins, an extraction of 2 g food/20 ml of 40% aqueous ethanol, and a minimal sample dilution of 1:20, a gliadin content as low as 2.4 ppm (or 4.8 ppm gluten) can be detected.

IgG Subclass Typing and Sequencing of the Anti-Gliadin and Anti-LMW Glutenin mAb Subclasses of the different mAb used in the competition assay were determined by an isotyping dipstick method. Except for the anti-LMW-glutenin-1 which is of the IgG3κ subclass, all mAb were of the IgG1κ subclass. The antibodies were further characterized by sequencing of the antibody specific variable region of both the heavy and light chain. After translation of the DNA sequence into amino acid sequences the antibody specific CD1, CD2 and CD3 regions of both heavy and light chains could be determined (Table 3)

Definition of the Minimal Epitopes Recognized by the Anti-Gliadin mAb Used in the Different Competition Assays To define the minimal amino acid sequence still recognized by the anti Glia-[alpha]2/9 and the anti Glia-[gamma]1 mAb competition experiments were performed. For this, peptides were synthesized encoding sequences that overlap with the amino acid sequence used for generation of the mAb. The minimal amino acid sequence recognized by the anti-Glia-[alpha]2/9 mAb was LQPFPQPQ (SEQ ID NO: 20)(FIG. 5A) which covers most of the Glia-[alpha]9 T cell epitope. Similarly we found that the minimal sequence recognized by the anti-Glia-[gamma]1 mAb was QQRPFI (SEQ ID NO: 21) (FIG. 5B) which overlaps with the C-terminal amino acids of the Glia-[gamma]1 T cell epitope[9].

Definition of the Minimal Epitopes Recognized by the Anti-LMW Glutenin mAb Used in the Different Competition Assays To define the minimal amino acid sequence still recognized by the two anti-LMW-glutenin mAb competition experiments were performed. For this, peptides were synthesized encoding sequences that overlap with the amino acid sequence used for generation of the mAb. The minimal amino acid sequence recognized by the anti-LMW-glutenin-1 mAb was QSPFS (SEQ ID NO: 22) (FIG. 5C) which covers the C-terminal part of the Glt-156 T-cell epitope. Similarly we found that the minimal sequence recognized by the anti-LMW-glutenin-2 mAb was PPFSQQ (SEQ ID NO: 7) (FIG. 5D) which overlaps with the N-terminal amino acids of the Glt-156 T cell epitope[10].

Comparison of the Detection of T Cell Epitopes in Intact Gliadin Proteins with Detection of T Cell Epitopes in Peptides.

T cell stimulatory epitopes can be encoded by both small peptide fragments (down to 11 to 12 amino acids) and intact gluten proteins. To determine whether the new assays can detect T cell epitopes in both proteins and peptides, competition assays were performed with the European gliadin reference (IRMM-480)[26] containing intact gliadin proteins and synthetic peptides of 25 amino acids. For the Glia-α2/9 competition assay a difference was found between the detection of the peptides in intact proteins and the 25-mer synthetic peptide (FIG. 6A). A higher concentration of peptides is required to reach the same level of competition as found for intact proteins. This indicates that the affinity of the anti-Glia-α2/9 mAb is lower for peptides than for intact proteins. In contrast, for the Glia-γ1 and the LMW-glutenin competition assays no difference was found between the detection of the peptide in intact proteins and the 25 mer synthetic peptide (FIGS. 6B, 6C and 6D). Both are detected with similar sensitivity.

Figure 7:
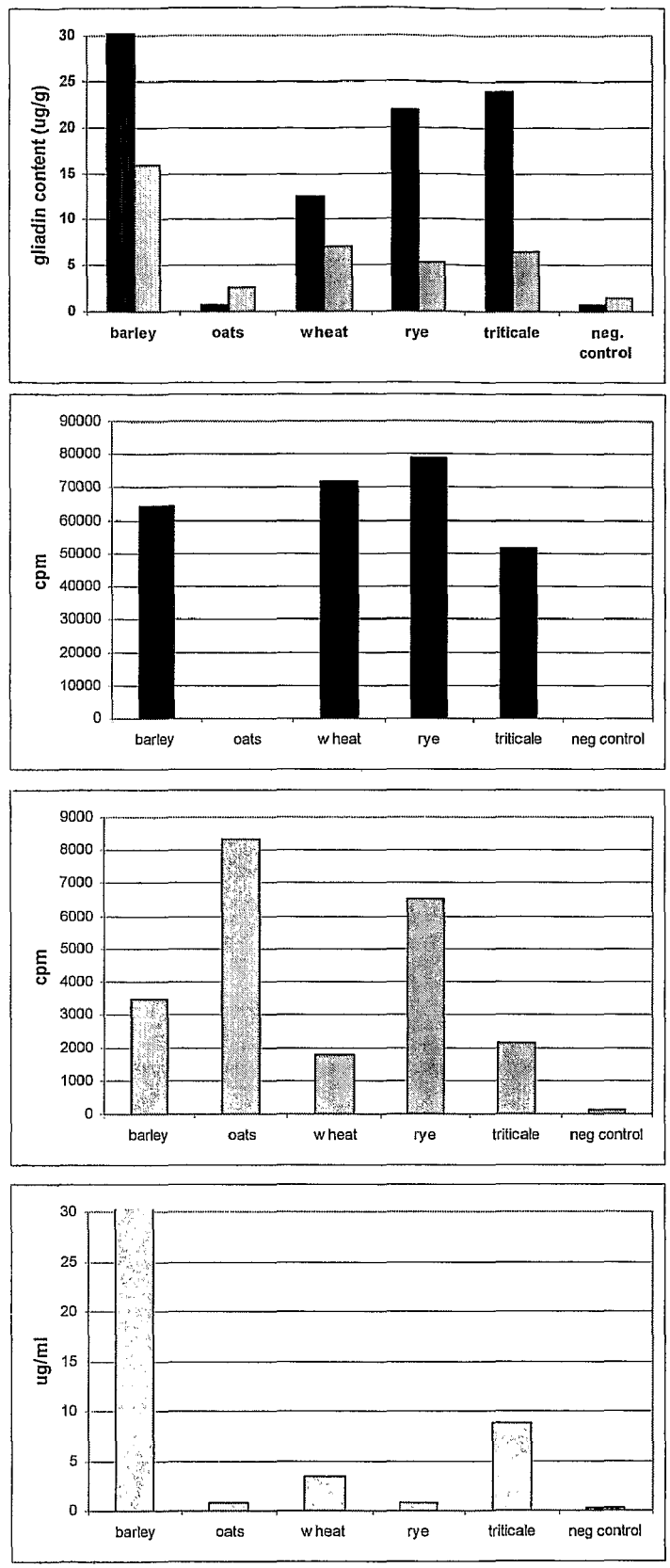

Detection of T Cell Stimulatory Epitopes in Cereals by the Competition Assay and Gliadin Specific T Cell Clones Next to wheat other cereals like barley, rye and oats also contain storage proteins that are homologues to gliadin. To test whether our method is suitable for the detection of gliadin homologues encoding T cell stimulatory epitopes in cereals other than wheat, protein extracts were made of barley, oats, wheat, rye and triticale (a hybrid of wheat and rye, used in the food industry). The extracts were measured both in the competition assays for α-, γ-gliadin and LWM-glutenin and with one Glia-α2/9 and one Glia-γ1 specific T cell clone. For the gliadin, with both techniques a similar reactivity pattern towards the cereal preparations was observed. Both methods detected the Glia-α2/9 epitope in protein preparations of barley, wheat, rye and triticale, but not in oats (FIGS. 7A and B). Both methods, however, detected the Glia-γ1 T cell epitope not only in the cereals barley, wheat, rye and triticale but also in oats. (FIGS. 7A and C). The competition assays specific for the Glt-156 T cell epitope show that as for the gliadins, the Glt-156 T cell epitope could be detected clearly in the cereals barley, triticale and wheat and, although in much lower amounts, in oats and rye (FIG. 7D). This demonstrates that the new method is suitable to detect the presence or absence of not only T cell epitopes encoded by wheat gliadin and glutenin but also in gliadin and glutenin homologues of other cereals. This is likely to relate to the toxicity of these cereals for CD patients Analysis of Food Samples by the New Method For the detection of gliadin in food products and starch samples with known gluten content[28], ethanol extracts were prepared. These starch samples were included in the experiments to compare the results of the new method with those obtained by a commercial Elise. After a 20 to 40-fold dilution the gliadin content of the extracts was measured with the competition assays for the Glia-α2/9 and Glia-γ1 T cell epitopes.

The gliadin levels detected in commercial starch control samples with the new competition assays for α- and γ-gliadin correspond with the levels stated by the commercial Elisa kit[28] (Table 4). When measured in the ethanol extract of the food products, high levels of both α- and γ-gliadin could be detected in the products 11, 12 and 16 whereas low levels could be detected in food products 1, 2, 4, 13, 14 and 18. In a product in which maize starch (prod. no 15) was used, the levels of gliadin were very low (γ-gliadin) or not detectable (α-gliadin) Also with the competition assay for the detection of LMW-glutenin different levels of the Glt-156 epitope could be detected Like for the competition assays detecting T cell epitopes from α- and γ-gliadin the highest levels of the T cell epitope Glt-156 were measured in the foodproducts 11, 12 and 16. Significantly lower amounts of Glt-156 were detected in foodproducts 6, 8 and 9 (results not shown). Most of the values obtained with the new assays for α- and γ-gliadin are comparable with the values obtained with the commercial gluten detection kit. Moreover the results indicate that with the new assays more accurate values can be assigned. Moreover, a distinction can be made between α-, γ-gliadin and LMW glutenin which is not possible with the commercial gluten detection kit. These results indicate that the new competition assays are suitable for the detection of gluten in ethanol extracts of food samples. Differences in the levels of gliadin detected in a sample by the different assays can be explained by either the variation in the amounts of the proteins detected by the different assays or by the presence intact proteins together with small protein fragments.

Discussion

In this study a new method for the detection of gluten is described by which T cell stimulatory epitopes of α-, γ-gliadin (Glia-α2/9 and Glia-γ1 respectively) and LMW glutenin (Glt-156) can be detected. This method is the first antibody based method that can detect the presence of T cell stimulatory epitopes thought to be involved in the development of CD. Moreover, the method detects the Glia-α2/9, Glia-γ1 and Glt-156 T cell epitopes separately, and thus allows for discrimination between the presence of α-, γ-gliadin and LMW glutenin proteins in a sample.

For the development of the method mAb were generated specific for the Glia-α2/9, the Glia-γ1 and the Glt-156 T cell epitopes. Of the many mAb obtained, only 5 mAb were found to be suitable for sensitive competition assays for the detection of T cell stimulatory epitopes of gluten in different background. Because two of these mAb were found to have the same specificity, four mAb were selected to develop the competition assays. The minimal amino acid sequence recognized by the mAb was found to be smaller than the minimal T cell epitopes[9, 29, 30]. The sequence detected by the anti-Glia-γ1 mAb overlaps with the C-terminal part of the Glia-γ1 T cell epitope. For the anti-Glia-α2/9 mAb the minimal recognition sequence is contained within the T cell epitope and actually resides within the Glia-α9 peptide. Although this latter peptide is not recognized by al CD patients[29], the Glia-α2 and Glia-α9 peptides are partially overlapping and most patients respond to either one of these peptides[10, 29]. Detection of the sequence within the Glia-α9 peptide with our competition assay will thus also indicate the presence of the Glia-α2 peptide within the test sample. For both anti-Glt-156 mAb's the minimal recognition sequences reside within the Glt-156 peptide. The anti-LMW glutenin mAb (1) binds in the C-terminal part and the anti-LMW-glutenin mAb (2) binds in the N-terminal part of the T cell epitope.

With the mAb competition assays were developed. In a competition assay gluten epitopes in a sample compete for binding to a mAb with a biotinylated indicator peptide. Binding of the latter is detected. The advantage of a competition assay, in which only one mAb is used for the detection, is that both intact proteins and small protein fragments can be detected. This is not possible with the currently used sandwich Elisa systems[25,28]. These sandwich Elisa based system can only detect the presence of intact or rather large gluten fragments[25,28] since small fragments can not simultaneously be bound by two antibodies. These methods are therefore incapable of detecting the small gluten peptides that suffice for T cell stimulation.

Although our method is suitable for the detection of both intact proteins and protein fragments, the affinity of the Glia-α2/9 specific mAb is higher for the intact protein. In contrast, the anti-Glia-γ1 and the two anti-LMW glutenin mAb have a comparable affinity for intact proteins and protein fragments. Suitable standards must therefore be incorporated to ensure the accurate determination of both α-, γ-gliadin and LMW glutenin in test samples.

The ability to measure the presence of small gluten fragments is a major advantage since gluten hydrolysates and wheat starch hydrolysates are widely used in the food industry. These hydrolysates are obtained by enzymatic or chemical treatment and result in smaller constituents, primarily sugars, peptides and amino acids. Since peptides with sizes of 11 amino acids only are large enough to stimulate T cells, it is important to ensure the absence of such remaining peptides in food products and in gluten free food products in particular.

The competition assay could detect both the Glia-α2/9, the Glia-γ1 and the LMW glutenin T cell epitopes in ethanol extracts of food samples containing wheat flour or wheat starch. In food samples in which maize starch was used neither α-gliadin nor LMW glutenin and only a very small amount of γ-gliadin was detected. The gliadin levels measured in the control starch samples were comparable with the levels detected by a commercial gluten assay. With a detection limit of 12.5 ng/ml for the European gliadin standard and a minimal dilution of 1:20 for the ethanol extraction samples (1 g/10 ml), our assay can detect both α- and γ-gliadins at a level of 2.5 ppm which corresponds with 5 ppm of gluten. For the assays detecting LMW glutenin a detection level between 2.5-5 ppm of the European gliadin standard (also containing glutenins) could be detected probably corresponding to 5-10 ppm of gluten. These detection limits are well below the 20 ppm threshold for gluten in gluten free products proposed by the Codex Alimentarius Commission. Therefore the new method is suitable for screening of food products recommended for a gluten free diet for the presence of T cell stimulatory epitopes.

Moreover, when protein preparations of different cereals were tested with our new method, different levels of α-, γ-gliadin and LMW glutenin could be detected in barley, wheat, rye, triticale and oats. This result indicate that the mAb's not only detect the T cell epitopes present in gliadin but also those present in other homologous proteins like the hordeins of barley, the secalins of rye and the avenins of oats. This broad cross reactivity of the mAb is a major advantage compared to already existing gluten detection methods since the mAb used in a commercial assay for the detection of ω-gliadin only low cross reactivity was found with the hordeins and no cross-reactivity with the avenins[24]. Moreover, with an assay detecting α-, γ- and ω-gliadin no cross-reactivity with avenin was detected[25].

Until recently, oats was considered relatively safe for CD patients. This because of the predicted low number of T cell stimulatory sequences[15, 30 31 323], and studies which showed that most CD patients tolerate the introduction of oats into their diet[33 32 34 30 35 36 37 38 39 40 1]. In the present invention, however, we demonstrate that both with the new method and with gliadin specific T cell clones, T cell stimulatory epitopes axe not only abundant in barley, wheat, rye and triticale, but some epitopes can also be found in oats (in particular the Glia-γ1 T cell epitope). In line with the recent reports on reactions of CD patients to oats, our and other results[41 42] suggest that oats may not be safe for all CD patients.

Finally, our study further emphasizes the need for new cereals lacking T cell stimulatory epitopes. Although there is no evidence for the existence of cereals that lack toxicity for CD patients, our new method may be a useful tool for the selection of wheat varieties that contain less of the harmful T cell stimulatory gluten peptides. Such varieties may open the way to the breeding and/or development of cereals that are safer for consumption by patients. In conclusion we have developed a mAb based method for the detection of T cell stimulatory epitopes known to be involved in CD. The new method has many advantages compared to the existing methods for the detection of gluten since it is the first method that can detect; (i) T cell stimulatory epitopes; (ii) α-, γ-gliadin and LMW glutenin separately; (iii) T cell stimulatory epitopes present on gliadin and LMW glutenin homologues present in other cereals also known to be involved in CD; (iv) T cell stimulatory epitopes on both intact proteins and small protein fragments. The new method will be a valuable tool in the screening of food products that are intended to be used in the gluten free diet of CD patients.

Example 2

Materials and Methods

Database Searches

A wheat gliadin and glutenin subset was extracted from the Uniprot database using the SRS program (www.ebiac.uk). All epitope sequences listed in Table 5 were searched for full similarity against this subset using the stand-alone Macintosh version of the program PeptideSearch (http://www.mann.embl-heidelberg.de/GroupPages/PageLink/peptidesearchpage.html.)

Description of the Different Wheat Accessions

The wheat accessions used in this study were obtained from the small grain cereal collection maintained by the Centre for Genetic Resources (CGN, Wageningen, The Netherlands). The wheat accessions used in this study were selected on the basis of the species known to have played a role in the evolution of bread wheat, and they include all three genomes of the most important cereal crop in the world. Di-, tetra- and hexaploid accessions were used (Table 6). The accessions were selected from a small-grain cereal collection which contains well over five thousand wheat accessions. The selection criteria were: difference in (1) genetic background, (2) ploidy level, (3) geographic distribution and (4) growth season (Table 6).

Preparation of Gluten Containing Samples from Different Wheat Varieties

Samples of different wheat varieties were grinded and a trypsin/pepsin digest was prepared as follows: 2 g of wheat flour was solubilized in 20 ml 1M acetic acid and boiled for 10 minutes. After cooling, 10 mg pepsin A (Sigma P-7012, Sigma Chemical Co, St Louis, USA) was added and the mixture was incubated for 4 hours at 37° C. Subsequently the pH was adjusted to 7.8 with NaOH, followed by addition of 20 mg trypsin (Sigma T-4665). After overnight incubation at 37° C., trypsin inhibitor type II (Sigma) was added and the sample was dialysed against water for 48 hours. The dialysate was centrifuged and the supernatant fractionated over a 30 kD membrane (Centriprep YM-30, Amicon Inc., Beverly, USA). For the subsequent experiments the fraction smaller than 30 kD was used. A control sample was prepared from a commercial gliadin preparation (Fluka Chemie no. 48960, Zwijndrecht, the Netherlands) using the same protocol. For the T cell assay the pepsin/trypsin digests were treated with tissue transglutaminase as described (11).

T Cell Proliferation Assays

To test for the presence of T cell stimulatory epitopes in different wheat varieties six different T cell clones each recognizing a different epitope were used: a Glia-α2/9-specific T cell clone, (recognizing both the Glia-α2 and Glia-α9 T cell epitope), a Glia-γ1-specific T cell clone, a Glia-γ30-specific T cell clone, a LMW-Glt-156-specific T cell clone, a LMW-Glt-17-specific T cell clone and a HMW-glutenin-specific T cell clone. The clones originate from gluten-specific T cell lines generated from small intestinal biopsies of different coeliac disease patients (10; 12; 14; 15). With the exception of the HLA-DQ8 restricted, HMW-glutenin specific T cell clone, all T cell clones are HLA-DQ2 restricted. For the HLA-DQ2 restricted T cell clones the pepsin/trypsin digests of the different wheat varieties were treated with tissue transglutaminase (tTG) to facilitate T cell recognition of the T cell stimulatory gluten peptides (14; 50).

Proliferation assays were performed in triplicate in 150 µl Iscove's Modified Dulbecco's Medium (Bio Whittaker, Verviers, Belgium) with 10% pooled normal human serum in 96 well flat-bottom plates using $10^4$ gluten specific T cells stimulated with $10^5$ irradiated HLA-DQ2- or HLA-DQ-8- (HMW glutenin) matched allogeneic peripheral blood mononuclear cells (3000 rad) in the presence or absence of antigen (1-104 ml). After 2 days $^3$H-thymidine (0.5 µCi/well) was added to the cultures, and 18-20 hours thereafter cells were harvested. $^3$H-thymidine incorporation in the T cell DNA was counted on a liquid scintillation counter (1205 Betaplate Liquid Scintillation Counter, LKB Instruments, Gaithersburg, Md.). For the detection of IFN-γ production 50 µl supernatant was collected from the cultures before the addition of 3H-thymidine. IFN-γ production was measured using the Cytometric Bead Array (Becton Dickinson, San Diego, USA). The experiment was repeated twice for each T cell clone.

Synthetic Peptides

Peptides were synthesized by standard Fmoc chemistry on a SyroII peptide synthesizer. The integrity of the peptides was checked by rpHPLC and mass spectrometry. The S-acetylmercaptoacetic acid (SAMA) group was introduced in the resin-bound peptides by coupling of a 6-fold equimolar mixture of S-acetyl mercaptoacetic acid N-hydroxysuccinimide ester and 1-hydroxybenzotriazole in NMP during two hours. Biotin was introduced in the resin-bound peptides by a two hour coupling with a 6-fold equimolar preactivating mixture of biotin and PyBop mAb Against T Cell Stimulatory Epitopes of Low Molecular Weight (LMW) and High Molecular Weight (HMW) Glutenin Proteins For generation of inAbs specific for the LMW-glutenin derived T cell stimulatory epitope Glt-156, mice were immunized with peptides chemically crosslinked to tetanus toxoid (TTd-DDDXPPFSQQQQSPFS (SEQ ID NO: 23)-amide). For generation of mAb specific for the HMW glutenin derived T cell stimulatory epitope presented by HLA-DQ8 molecules, peptides chemically cross-linked to tetanus toxid (TTd-DDDXPGQGQ(Q/P)GYYPTS(L/Q)QQP (SEQ ID NO: 24)-amide and TTd-DDDXQGQQGYYPTSPQQ(P/S) (SEQ ID NO: 25)-ar[alpha]ide were used for immunization. Fusion and screening of the hybridoma's was performed as described (49).

Competition Assays for the Quantitative Detection of T Cell Stimulatory Epitopes of Gluten Proteins.

Competition assays were performed as described earlier (49). For the competition assay detecting LMW-glutenin a biotinylated peptide encoding the LMW-Glt-156 T cell epitope was used as the indicator peptide (Bio-XKAKAKAXPPFSQQQQSPFS (SEQ ID NO: 26)-amide). For the competition assay detecting HMW-glutenin a biotinylated peptide encoding the HMW-glutenin epitope was used as the indicator peptide (Bio-XKAKAKAKAX- QGQQGYYPTSPQQP (SEQ ID NO: 27)-amide). For quantification of the gliadin and LMW-glutenin assays a standard curve was made by the European gliadin reference IRMM-480 (26) in a concentration range of 100 [mu]g/ml-3 ng/ml. For the HMW-glutenin assay a standard curve was made using a trypsin/chymotrypsin digest of recombinant HMW-glutenin proteins (kindly provided by P. Shewry, Rothamsted Research, Hampenden, United Kingdom) in a concentration range from 10 [mu]g/ml-10 ng/ml. The assays were repeated twice.

Protein Analysis by 1D SDS-PAGE, Western Blotting

For protein analysis wheat grains were grinded and the wheat flour was resuspended in 8 M Urea, 10 mM Tris HCl pH 8.0. After one hour head over heel rotation the wheat flour suspensions were spun down and the soluble fraction was used for 1D SDS-PAGE.

SDS-PAGE (12.5% acrylamide gel) was performed under standard conditions. After separation proteins were either stained with Coomassie Brilliant Blue or transferred to nitrocellulose. On the blots proteins were visualized with monoclonal antibodies specific for stimulatory T cell epitopes from α- and γ-gliadin (49) and LMW-glutenin (this example).

Results

Matching of Gliadin and Glutenin Derived T Cell Epitopes with Gluten Proteins

It is unknown if all gluten genes are equally toxic for CD patients. The sequences of hundreds of gluten proteins are available through databases. We have now aligned the sequence of eleven T cell stimulatory sequences from α-gliadin, γ-gliadin, LMW- and HMW-glutenin with the gliadin and glutenin proteins present in the Uniprot database (Table 5). Strikingly, while all γ-gliadins contained one or more T cell stimulatory sequences, the large majority of the LMW-glutenin and one-third of the α-gliadin proteins did not contain the T cell-stimulatory epitopes searched with (Table 7). Also, some of the HMW-glutenin proteins contained no or a few T cell-stimulatory sequences. The results also indicate that while some gluten proteins lack T cell stimulatory sequences, others may contain up to six. Thus, considerable variability in toxicity of individual gluten proteins is likely to exist.

Detection of T Cell Stimulatory Epitopes by T Cell Based Assays

We have previously described T cells specific for T cell stimulatory epitopes in a-gliadin, g-gliadin and LMW-glutenin (10; 14; 15). We have used these T cells to screen wheat accessions for the presence of these epitopes. For this, 16 wheat accessions were selected (Table 6). Pepsin/trypsin digests of grinded seeds of these Triticum accessions were prepared, treated with tissue transglutaminase, and tested with T cell clones specific for the Glia-α2/9, Glia-γ1, Glia-γ30, LMW-Glt-17 and LMW-Glt-156 peptides. The results reveal striking differences in the T cell responses to the individual wheat preparations. Representative results are shown in FIGS. 8A and D and a summary of all results is given in Table 8. Wheat varieties either induced low, medium or high T cell responses, independent of the ploidy level or genome background of the accessions (Table 8; FIGS. 8A and D). Very low responses were found for the diploid accession #4 and the hexaploid accessions #13 and #16 (Table 8). Next we determined if the observed differences in proliferative T cell responses correlated with similar differences in IFN-γ production. An α-gliadin and a LMW-glutenin T cell clone were tested against proteins extracts from the wheat accessions #4, #9, #10, #13, #14, and #16 and T cell proliferation and IFN-γ production were measured simultaneously. In all cases a clear correlation was found between T cell proliferation (FIGS. 9A and C) and IFN-γ production (FIGS. 9B and D). Together these results indicate that wheat varieties differ significantly in the level of T cell stimulatory epitopes present.

Detection of T Cell Stimulatory Epitopes by mAb Based Competition Assays

Subsequently, pepsin/trypsin digests of grinded seeds of the Triticum accessions were tested with monoclonal antibodies (mAb) specific for the T cell epitopes Glia-α9, Glia-γ1 (49) and LMW-Glt-156 (this example) in a competition assay as described. (49). In agreement with the results of the T cell assay, we observed large differences in the levels of the three gluten epitopes in the wheat accessions tested (Table 8; FIGS. 8B and E). Also with this assay we observed that varieties #4 and #13, and #16 contain low levels of the gluten peptides (Table 8). These results thus confirm the results of the T cell based assay and indicate that not all varieties contain similar amounts of T cell stimulatory gluten sequences.

Western Blot Analysis of Gluten Proteins in Wheat Accessions

The α-gliadin and LMW-glutenin specific mAb are also suitable for the specific detection of α-gliadins and LMW-glutenins on Western blots. We have therefore used these mAb to stain gluten proteins expressed in the wheat accessions. Protein extracts were prepared from five wheat accessions that were found to contain different amounts of the T cell stimulatory epitopes in the T cell and mAb based competition assays: varieties #6 (diploid, DI) genome), #7, #9, and #10 (tetraploid, AABB), and #14 (hexaploid, AABBDD). Next, the proteins were separated by one-dimensional SDS-PAGE and, after blotting onto nitrocellulose membrane, stained with the mAb used in the competition assays (FIGS. 8C and F). With the LMW-glutenin mAb staining was observed for all but the diploid. (DD) accession #6 (FIG. 8C). In this accession relatively low levels of the LMW-glutenin derived T cell stimulatory epitope were detected with both the T cell- and the mAb-based assay (FIGS. 8A and B). Moreover, in the accessions #7 and #9 the antibody stained a protein that was distinct from that in accessions #14 and #10. This correlates, with the presence of an intermediate level of the T cell stimulatory glutenin epitopes in the accessions #7 and #9, as compared to a high level of the T cell stimulatory epitopes in accessions 10 and 14 (FIGS. 8B and C). With the α-gliadin specific mAb staining was found for all accessions. However, a distinct staining pattern was obtained for each variety, indicating the presence of different gliadin proteins in the accessions (FIG. 8F). Together these results indicate that the observed differences in the levels of T cell stimulatory epitopes found in the wheat varieties are caused by differences in protein composition between the wheat accessions.

Detection of a T Cell Stimulatory HMW-Glutenin Peptide in Wheat Accessions

Figure 10:
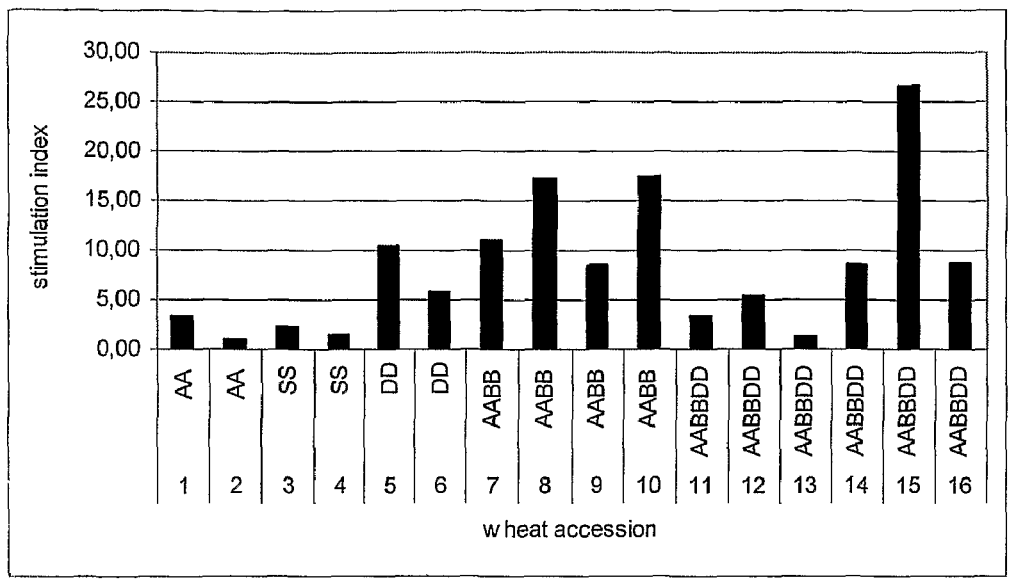
Figure 10:
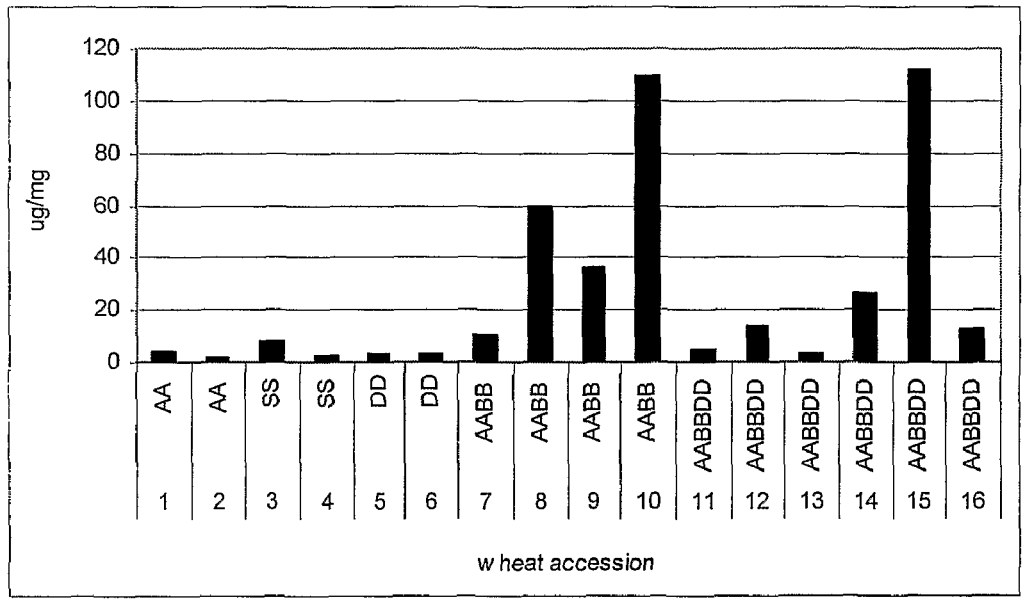

The baking quality of wheat derived flours to a large extent depend on the presence of HMW-glutenins. These HMW-glutenins have long been considered 1.5 not to be involved in CD but recent evidence has indicated that also the HMW-glutenins contain T cell stimulatory peptides (12, 13) although only one such peptide has been identified at present (12). We have therefore also tested the pepsin/trypsin digest of the wheat accessions with a T cell clone specific for this HMW-glutenin peptide (12) and a mAb raised against this peptide (this example). In this case the digests were not treated with tissue transglutaminase as both the T cell clone and the mAb preferentially respond to native HMW-glutenin (12 and not shown). The results (FIG. 10, Table 8) show that large differences exist in the presence of the HMW-glutenin peptide. The lowest values are found in the AA and SS diploid accessions and in some of the tetraploid accessions. Thus, in addition to the gliadins and LMW-glutenins, considerable variability exist with regard to the presence of the HMW-glutenin peptide in the wheat accessions.

Discussion

The results indicate that large differences exist with regard to the presence of T cell stimulatory gluten peptides in the wheat accessions investigated, independent of the ploidy level. To further substantiate these observations a large number of gluten genes present in public databases was screened for the presence of eleven T cell stimulatory sequences. In agreement with the result of our T cell and mAb screening, a surprisingly large number of gluten genes were found to lack the T cell stimulatory sequences searched with. About one-third of the α-gliadin genes encodes proteins that lacked T cell stimulatory sequences and a large proportion of the LMW-glutenins was also found to lack the T cell stimulatory sequences. It should be noted that this does not implicate that such gluten proteins may not have any T cell stimulatory properties. They may contain a variant of the T cell stimulatory sequence searched with, and some of such variants may have T cell stimulatory properties. In contrast to the α-gliadins and LMW-glutenins the majority of HMW-glutenins and all of the γ-gliadins were found to contain T cell stimulatory sequences. Together, these results indicate that individual gluten proteins are likely to have a distinct toxicity profile.

Using a method of the present invention it is thus possible to select for variants that have absent or low amounts of specific T cell stimulatory sequences. The present invention therefore provides the use of a variant that has no or low amounts of a specific T cell stimulatory sequence for the production of a food or an ingredient therefore.

Several studies have suggested that the α-gliadins encode the immunodominant T cell response inducing gluten peptides while the γ-gliadins and glutenins have received much less attention (29; 52). In the present invention, however, the γ-gliadins appear to most frequently contain T cell stimulatory sequences. It is therefore easier to select wheat varieties that lack harmful α-gliadins as γ-gliadins. Wheat varieties lacking harmful α-gliadins are therefore preferred in the present invention.

Although the γ-gene clusters seem less diverse composition of the γ-gliadin gene clusters is sufficiently diverse to allow the identification of clusters that are completely free of toxic peptides. In this respect it is worth noting that varieties #4, #13 and #16 appear to contain low levels of all peptides tested for, including the γ-gliadin peptides. Apparently, depending on which γ-gliadin genes are actually expressed, considerable differences in protein composition is present between the varieties and this may be exploited to select for varieties that contain low levels of T cell stimulatory γ-gliadin peptides. Alternatively, silencing of the entire γ-gliadin gene locus may be used to remove γ-gliadin-related toxicity from wheat accessions. Such an approach would be less favored for the LMW- and the HMW-glutenins as they are important for the baking quality of wheat based doughs.

It is known that early exposure to gluten and a double HLA-DQ2 gene dose both promote CD development. In Sweden the addition of gluten to infant food led to a 5-fold increase in the occurrence of CD in the 1980's (51) and HLA-DQ2 homozygous individual have a fivefold increased risk of developing disease compared to HLA-DQ2 heterozygous individuals (53). A large repertoire of abundant immunogenic gluten peptides in the diet, together with a high copy number of HLA-DQ2, thus favors the breaking of oral tolerance (54). In present day practice, gluten is introduced into the diet of infants at age 6-7 months. As there is no restriction in the amount of gluten given, gluten intake at age 12 months is between 6 and 9 grams daily (54) while gluten-specific T cells of CD patients are known to respond to microgram amounts. The sudden introduction of grams of gluten may thus play an important role in the breaking of oral tolerance. The current understanding of the development of the disease may call for a more gradual and/or reduced intake of gluten in infants (55). The breeding of wheat varieties with a lower amount of T cell stimulatory gluten peptides would potentially aid in reaching that goal.

In the present invention it was found that the α-gliadin peptide in the AA and BB/SS genome is low to absent presence of. Similarly, we observed a variability in the presence of gamma-gliadin derived peptides.

We have also analysed six wheat varieties that are typically used for bread making and that contain three genomes: AABBDD. Moreover, we have also analysed the presence of LMW- and HMW-glutenin derived peptides and demonstrate considerable heterogeneity in the levels of these peptides in the wheat accessions as well. We feel that this is particularly relevant as the HMW-glutenins are a major factor determining the baking quality of wheat flour and we have previously reported that T cell responses to LMW-glutenins are frequently observed in children (10).

In conclusion, our data demonstrate that with the use of gluten-specific T cells and/or mAb directed to T cell stimulatory gluten peptides, wheat accessions can be selected that contain minimal to absent quantities of particular harmful gluten sequences. Thus new varieties can be bred that will be acceptable for manufacturing of food products for CD patients. Moreover such varieties may prove to be valuable tools for disease prevention in individuals at risk.

REFERENCES

1. Dicke W K, Weijers, H A, and Van de Kamer, J H. Coeliac Disease II. The presence in wheat of a factor having a deleterious effect in cases of coeliac disease. Acta Paediatr. 1952; 42:34-42.
2. Marsh M N. Gluten, major histocompatibility complex, and the small intestine. A molecular and immunobiologic approach to the spectrum of gluten sensitivity ('celiac sprue'). Gastroenterology 1992; 102:330-354.
3. Molberg O, Kett, K, Scott, H et al. Gliadin specific, MA DQ2-restricted T cells are commonly found in small intestinal biopsies from coeliac disease patients, but not from controls [corrected and republished article originally printed in Scand J Immunol 1997 July; 46(1):103-8]. Scand. J. Immunol. 1997; 46:103-109.
4. Jensen K, Sollid, LM, Scott, H et al. Gliadin-specific T cell responses in peripheral blood of healthy individuals involve T cells restricted by the coeliac disease associated DQ2 heterodimer. Scand. J. Immunol. 1995; 42:166-170.
5. Lundin S E, Scott, H, Fausa, O et al. T cells from the small intestinal mucosa of a DR4, DQ7/DR4, DQ8 celiac disease patient preferentially recognize gliadin when presented by DQ8. Hum. Immunol. 1994; 41:285-291.
6. Gjertsen H A, Lundin, KE, Sollid, L M et al. T cells recognize a peptide derived from alpha-gliadin presented by the celiac disease-associated HLA-DQ (alpha 1*0501, beta 1*0201) heterodimer Hum. Immunol. 1994; 39:243-252.
7. Lundin K E, Scott, H, Hansen, T et al. Gliadin-specific, HLA-DQ (alpha 1*0501, beta 1*0201) restricted T cells isolated from the small intestinal mucosa of celiac disease patients. J. Exp. Med. 1993; 178:187-196.
8. Paulsen G, Lundin, KE, Gjertsen, HA. et al. HLA-DQ2-restricted T-cell recognition of gluten-derived peptides in celiac disease Influence of amino acid substitutions in the membrane distal domain of DQ beta 1*0201. Hum. Immunol. 1995; 42:145-153.

9. Sjostrom H, Lundin, KE, Molberg, O et al. Identification of a gliadin T-cell epitope in coeliac disease: general importance of gliadin deamidation for intestinal T-cell recognition. Scand J. Immunol. 1998; 48:111-115.

10. Vader W, Kooy, Y, van Veelen, P et al. The gluten response in children with celiac disease is directed toward multiple gliadin and glutenin peptides. Gastroenterology 2002; 122:1729-1737.

11. Van de Wal Y, Kooy, Y M, van Veelen, P A et al. Small intestinal T cells of celiac disease patients recognize a natural pepsin fragment of gliadin. Proc. Natl. Acad. Sci. U.S.A 1998; 95:10050-10054.

12. Van de Wal Y, Kooy, YM, van Veelen, P et al. Glutenin is involved in the gluten-driven mucosal T cell response. Eur. J. Immunol 1.999; 29:3133-3139.

13. Molberg O, Solheim, F N, Jensen, T et al. Intestinal T-cell responses to high-molecular-weight glutenins in celiac disease. Gastroenterology 2003; 125:337-344.

14. Van de Wal. Y, Kooy, Y, van Veelen, P et al. Selective deamidation by tissue transglutaminase strongly enhances gliadin-specific T cell reactivity. J. Immunol. 1998; 161: 1585-1588.

15. Vader L W, De Ru, A, Van der Wal Y et al. Specificity of tissue transglutaminase explains cereal toxicity in celiac disease. J. Exp. Med. 2002; 195:643-649.

16. Fleckenstein B, Molberg, O, Qiao, S W et al. Gliadin T Cell Epitope Selection by Tissue Transglutaminase in Celiac Disease. J. Biol. Chem. 2002; 277:34109-34116.

17. Molberg O, McAdam, S, Lundin, K E et al. T cells from celiac disease lesions recognize gliadin epitopes deamidated in situ by endogenous tissue transglutaminase. Eur J Immunol. 2001; 31:1317-1323.

18. Molberg O, Kett, K, Scott, H et al. Gliadin specific, HLA DQ2-restricted T cells are commonly found in small intestinal biopsies from coeliac disease patients, but not from controls [corrected and republished in Scand J Immunol 1997 September; 46(3):103-9]. Scand. J. Immunol. 1997; 46:103-108.

19. Spurkland A, Ingvarsson, G, Falk, E S et al. Dermatitis herpetiformis and celiac disease are both primarily associated with the HLA-DQ (alpha 1*0501, beta 1*02) or the HLA-DQ (alpha 1*03, beta 1*0302) heterodimers. Tissue Antigens 1997; 49:29-34.

20. Spurkland A, Sollid, LM, Ronningen, K S et al. Susceptibility to develop celiac disease is primarily associated with HLA-DQ alleles. Hum. Immunol. 1990; 29:157-165.

21. Solid L M, Markussen, G, Ek, J et al. Evidence for a primary association of celiac disease to a particular HLA-DQ alpha/beta heterodimer. J. Exp. Med. 1989; 169:345-350.

22. Report of the 25th Session of the Codex Alimentarius Committee on Nutrition and Foods For Special Dietary Uses, Bonn 2003."

23. Shewry P R and Halford, NG. Cereal seed storage proteins: structures, properties and role in grain utilization. J. Exp. Bot. 2002; 53:947-958.

24. Skerritt J H and Hill, A S. Enzyme immunoassay for determination of gluten in foods: collaborative study. J. Assoc. Off Anal. Chem. 1991; 74:257-264.

25. Valdes I, Garcia, E, Llorente, M et al. Innovative approach to low-level gluten determination in foods using a novel sandwich enzyme-linked immunosorbent assay protocol Eur. J. Gastroenterol. Hepatol. 2003; 15:465-474.

26. Eckert R Van. The PWG gliadin, a new reference material. Proceedings of the 16th meeting Working Group on Prolamin Analysis and Toxicity. Sitges, Spain 2000.

27. Hack C E, Paardekooper, J, Smeenk, R J et al. Disruption of the internal thioester bond in the third component of complement (C3) results in the exposure of neodeterminants also present on activation products of C3. An analysis with monoclonal antibodies J. Immunol. 1988; 141:1602-1609.

28. Tepnel Biosystems. Gluten assay kit, for the quantitative determination of gluten in food products by enzyme immunoassay (Tepnel Life Sciences, Flintshire, United Kingdom).

29. Arentz-Hansen H, Korner, R, Molberg, O et al. The intestinal T cell response to alpha-gliadin in adult celiac disease is focused on a single deamidated glutamine targeted by tissue transglutaminase. J. Exp. Med. 2000; 191:603-612.

30. Fraser J S, Engel, W, Ellis, H J et al. Coeliac disease: in vivo toxicity of the putative immunodominant epitope. Gut 2003; 52:1698-1702.

31. Hoffenberg E J, Haas, J, Drescher, A et al. A trial of oats in children with newly diagnosed celiac disease. J. Pediatr. 2000; 137:361-366.

32. Janatuinen E K, Kemppainen, TA, Pikkarainen, P H et al. Lack of cellular and humoral immunological responses to oats in adults with coeliac disease. Gut 2000; 46:327-331.

33. Janatuinen E K, Kemppainen, T A, Julkunen, R J et al. No harm from five year ingestion of oats in coeliac disease. Gut 2002; 50:332-335.

34. Janatuinen Eli, Pikkarainen, P H, Kemppainen, T A et al. A comparison of theta with and without oats in adults with celiac disease. N. Engl. J. Med. 1995; 333:1033-1037.

35. Picarelli A, Di Tola, M, Sabbatella, L et al. Immunologic evidence of no harmful effect of oats in celiac disease. Am. J. Clin. Nutr. 2001; 74:137-140.

36. Storsrud S, Hulthen, L R, and Lenner, R A. Beneficial effects of oats in the gluten-free diet of adults with special reference to nutrient status, symptoms and subjective experiences. Br. J. Nutr. 2003; 90:101-107.

37. Storsrud S, Olsson, M, Arvidsson, L R et al. Adult coeliac patients do tolerate large amounts of oats. Eur. J. Clin. Nutr. 2003; 57:163-169.

38. Janatuinen E K, Kemppainen, T A, Julkunen, R J et al. No harm from five year ingestion of oats in coeliac disease. Gut 2002; 50:332-335.

39. Picarelli A, Di Tola, M, Sabbatella, L et al. Immunologic evidence of no harmful effect of oats in celiac disease. Am. J. Clin. Nutr. 2001; 74:137-140.

40. Janatuinen E K, Kemppainen, T A, Pikkarainen, P H et al. Lack of cellular and humoral immunological responses to oats in adults with coeliac disease. Gut 2000; 46:327-331.

41. Srinivasan U, Leonard, N, Jones, E et al. Absence of oats toxicity in adult coeliac disease. BMJ 1996; 313:1300-1301.

42. Lundin K E, Nilsen, E M, Scott, H G et al. Oats induced vinous atrophy in coeliac disease, Gut 2003; 52:1649-1652.

43. Hollen E, Hogberg, L, Stenhammar, L et al. Antibodies to oat prolamines (avenins) in children with coeliac disease. Scand. J. Gastroenterol. 2003; 38:742-746.

44. Vader L W, Stepniak D T, Bunnik E M, Kooy Y M, De Haan W, Drijfhout J W, Van Veelen P A, Koning F. Characterization of cereal toxicity for celiac disease patients based on protein homology in grains. Gastroenterology 2003; 125:1105-1113.

45. Marti T, Molberg O, Li Q, Gray G M, Khosla C, Sollid L M. Prolyl Endopeptidase Mediated Destruction of T Cell Epitopes in Whole Gluten—Chemical and Immunological Characterization. J Pharmacol Exp Ther 2004.
46. Piper J L, Gray G M, Khosla C. Effect of prolyl endopeptidase on digestive-resistant gliadin peptides in vivo. J Pharmacol Exp Ther 2004.
47. Shan L, Molberg O, Parrot I, Haunch F, Filiz F, Gray G M, Sollid L M, Khosla C. Structural basis for gluten intolerance in celiac sprue. Science 2002; 297:2275-2279.
48. Anderson O D, J. C. Litts and F. C. Greene. The alpha-gliadin gene family I Characterization of ten new wheat alpha-gliadin genomic clones, evidence for limited sequence conservation for flanking DNA, and southern analysis of the gene family Theoretic Application Genetics 1997; 50-58.
49. Spaenij-Dekking E H, Kooy-Winkelaar E M, Nieuwenhuizen W F, Drijfhout J W, Koning F. A novel and sensitive method for the detection of T cell stimulatory epitopes of alpha/beta- and gamma-gliadin. Gut 2004; 53:1267-1273.
50. Molberg O, McAdam S N, Korner R, Quarsten H, Kristiansen C, Madsen L, Fugger L, Scott H, Noren O, Roepstorff P, Lundin K E, Sjostrom H, Solid L M. Tissue transglutaminase selectively modifies gliadin peptides that are recognized by gut-derived T cells in celiac disease. Nat Med 1998; 4:713-717.
51. Ivarsson A, Persson L A, Nystrom L, Ascher H, Cavell B, Danielsson L, Dannaeus A, Lindberg T, Lindquist B, Stenhammar L, Hernell O. Epidemic of coeliac disease in Swedish children. Acta Paediatr 2000; 89:165-171.

TABLE 1

| Gluten epitope | Peptide | | Conjugated |
|---|---|---|---|
| Glia-α2/α9 (61-71) | DDDXFPQPLPYPQP-amide | (SEQ ID NO: 28) | TTd |
| (59-69) | DDDXQPFPQPQLPYP-amide | (SEQ ID NO: 29) | TTd |
| (61-71) | RGRGRFPQPQLPYPQP-amide | (SEQ ID NO: 30) | BSA |
| (59-69) | RGRGRQPFPQPQLPYP-amide | (SEQ ID NO: 31) | BSA |
| Glia-γ1 (142-153) | DDDXPQQSFPQQQRPF-amide | (SEQ ID NO: 32) | TTd |
| (147-158) | DDDXPQQQRPFIQPSL-amide | (SEQ ID NO: 33) | TTd |
| (149-159) | DDDXQQRPFIQPSLQ-amide | (SEQ ID NO: 34) | TTd |
| (142-159) | RGRGRPQQSFPQQQRPFIQPSLQ-amide | (SEQ ID NO: 35) | BSA |
| Glt-156 (41-58) | DDDXPPFSQQQQSPFS-amide | (SEQ ID NO: 23) | TTd |
| (41-58) | RGRGRPPFSQQQQSPFS | (SEQ ID NO: 36) | BSA |
| HMW-glutenin | DDDXPGQGQ(Q/P)GYYPTS(L/Q)QQP-amide | (SEQ ID NO: 24) | TTd |
| HMW-glutenin | DDDXQGQQGYYPTSPQQ(P/S)-amide | (SEQ ID NO: 25) | TTd |

Peptides used for immunization of mice and detection of antibody producing hybridoma's. (X=aminohexanoyl spacer). Underlined are the amino acids that are part of the minimal epitope recognized by T cells[109]. HMW-glutenin peptides are collections of 4 and 2 peptides having the sequences as indicated and wherein the amino acids between brackets indicate the differences.

TABLE 2

| T cell epitope | biotinylated competitor peptide | |
|---|---|---|
| Glia α2/9 | BXKAKAKAKAXQPFPQPQLPYPQP-amide | (SEQ ID NO: 37) |
| Glia γ1 | BXAKAKAKAKXPQQSFPQQQRPFIQPSLQ-amide | (SEQ ID NO: 38) |
| Glt-156 | BXKAKAKAZPPFSQQQQSPFS-amide | (SEQ ID NO: 39) |
| HMW-glutenin | BXKAKAKAKAXQGQQGYYPTSPQQP-amide | (SEQ ID NO: 27) |

TABLE 3 amino acid sequence of hybridoma's

Variable region of IgG Heavy chain

| | leader | framework-1 | CD-1 | framework-2 |
|---|---|---|---|---|
| anti-[alpha]-gliadin: | MNLGLNWIFLVLVLKGVQC | EVKLVESGGGLVKPGGSLKLSCAASGFTFS | \|TYAMS\| | WVRQTPEKRLEWVA |
| anti-[gamma]-gliadin: | MDWVWNLPFLMAAAQSAQA | QIQLVQSGPELKKPGETVKISCKASGYTFT | \|NYGMN\| | WVKQAPGKGLKWMG |
| anti-LMW-glu1: | MDWVWXLXFLMAAAQSIQA | QIQLVQSGPELKKPGETVKISCKASGYTFT | \|NYGMN\| | WVKQAPGKGLKWMG |
| anti-LMW-glu2: | MDWVWNLLFLMAAAQTIQA | QIQLVQSGPEMKKPGETVKISCKASGYTFT | \|DYSMH\| | WVKEAPGKGLKWMG |
| anti-HMW : | MYLGLSCVIFIVFLLKGVQS | ELKLEESGGNLVQPGGSLKLSCLASGFSFT | \|KYWMN\| | WVRQSPERGLEWVG |

| | CD-2 | framework-3 | CD-3 | |
|---|---|---|---|---|
| anti-[alpha]-gliadin: | \|SISSGGSTTYYPDSVKG\| | RFTISRDNARNILYLQ MSSLRSEDTAMYYCAR | \|VPTYKD\| | YAMDYWGQGTSVTVSS (SEQ ID NO: 40) |

TABLE 3-continued amino acid sequence of hybridoma's

| | | | | |
|---|---|---|---|---|
| anti-[gamma]-gliadin: | \|WINTYTGEPTYADDFKG\| | RFAFSLEISASTAYLQ INNLKNEDMATYFCAK | \|TATYI\| | YAMDYWGQGTSVTAAAKT (SEQ ID NO: 41) |
| anti-LMW-glu1: | \|WINTNTGEPAYAEEFKG\| | RFAFSLETSASTAYLQ INNLKNEDTATYFCAR | \|SGY\| | YPFAYWGQQTLVTVSAAT TTAPXVPLAPGS(SEQ ID NO: 42) |
| anti-LMW-glu2: | \|WINTETAKPTYADDFRG\| | RFAFSLETSASTAYLQ INNLKNEDTATYFCSR | \|GIRD\| | YFDYWGQGTTLTVSSAKT TPPPVYPLAP(SEQ ID NO: 43) |
| anti-HMW : | \|EIRSKSDDYATHYAESVRG\| | RFTISRDDSKSSVYLQ MNNLRPEDAGIYYCSS | \|GTRG\| | YWGQGTTLTVSSAKTTPP SVYPLAPGSL(SEQ ID NO: 44) |

Variable region of Ig kappa Light chains

| | framework 1 | CD-I | framework 2C | CD-2 |
|---|---|---|---|---|
| anti-[alpha]-gliadin: | DVVMTQTPLSLPVSLGDQASISC | \|RSSQSLVHSNGNTYLH\| | WYLQKPGQSPKLLIY | \|KVSNRFS\| |
| anti-[gamma]-gliadin: | DIQMTQSPASLSASVGETVTITC | \|RASENIYSYLA\| | WYQQKQGKSPQILVY | \|DAKTLAD\| |
| anti-LMW-glu-1: | DIQMTQSPSSLSASLGERVSLTC | \|RASQDIGSSLN\| | WLQQEPDGTIKRLIY | \|LTSSLD\| |
| anti-LMW-glu-2: | DIVLTQSPASLAVSLGQRAPISC | \|RASKSVSKSGYNYMH\| | WYQQKPGQPPKLLIY | \|ASNLQS\| |
| anti-HMW: | HVVMTQAPLSLPVSLGDQVSISC | \|*STQSLVSDGDTFLN\| | WCLQKPGQSPNLLIY | \|KVSSRFA\| |

| | framework 3 | CD-3 | |
|---|---|---|---|
| anti-[alpha]-gliadin: | GVPDRFSGSGSGTDFTLKISRVEAEDLGVYFC | \|SQSTHVLT\| | FGAGTKLELKR(SEQ ID NO: 45) |
| anti-[gamma]-gliadin: | AVPSRFSGSGSGTHFSLKINSLQPEDFGSYYC | \|QHHYGSPLT\| | FGAGTKLELKR(SEQ ID NO: 46) |
| anti-LMW-glu-1: | GVPKRFSGSRSGSDYSLTISSLESEDFVDYYC | \|LQYASSPVT\| | FGAGTKLELKR(SEQ ID NO: 47) |
| anti-LMW-glu-2: | GVPARFSGSGSGTEFTLDIHPVEEEDAATYYC | \|QHSRELPFT\| | FGSGTKLEIKR(SEQ ID NO: 48) |
| anti-HMW: | GVPDRFTGSGSGTDFTLKISRVETEDLRVVF* | \|SQSSLVPRT\| | FGGGTKLVITR(SEQ ID NO: 49) |

TABLE 4

| Sample no | Content | Glia-α2/9 (μg/g) ppm | Glia-γ1 (μg/g) ppm | Gliadin content detected by commercial Elisa[28] (μg/g) ppm |
|---|---|---|---|---|
| low starch | <0.016% gluten[28] (≈<80 ppm of gliadin) | 1 | 7 | <75 |
| medium starch | 0.02-0.04% gluten[28] (≈100-200 ppm of gliadin) | 107 | 83 | 73 |
| high starch | >0.1% gluten[28] (≈>500 ppm of gliadin) | 889 | 421 | >1250 |
| 1 | starch | 4 | 28 | <75 |
| 2 | wheat starch | 1 | 20 | <75 |
| 4 | wheat flour | 18 | 51 | 227 |
| 6 | starch | 224 | 14 | 1174 |
| 11 | modified starch | 962 | 301 | >1250 |
| 12 | wheat flour | 11806 | 12593 | >1250 |
| 13 | modified starch | 13 | 37 | <75 |
| 14 | modified starch | 20 | 5 | <75 |
| 15 | modified starch (maize) | n.d. | 13 | <75 |
| 16 | wheat flour | 1540 | 1709 | 1711 |
| 18 | malt aroma | 152 | 59 | <150 |

Detection of presence of T cell stimulatory epitopes by the new assays for α- and γ-gliadin and by a commercially available gluten detection kit[28] in 40% aqueous ethanol extracts of commercial starch controls[28] and various food products. Gliadin levels were calculated using the European gliadin reference IRMM-480[26] as a standard.

TABLE 5

Amino acid sequences of previously identified T cell stimulatory epitopes of gluten used for sequence alignments with the gluten proteins present in the Uniprot database.

| HLA restriction | protein | epitope | reference |
|---|---|---|---|
| HLA DQ8 | α-gliadin | QGSFQPSQQ | (10) |
| | HMW-glutenin | QGYYPTSPQ | (17) |
| HLA DQ2 | α-gliadin | PFPQPQLPY (α-9) | (27) |
| | | PQPQLPYPQ (α-2) | (27) |
| | | FRPQQPYPQ (α-20) | (16) |
| | γ-gliadin | PQQSFPQQQ (γ-1) | (6) |
| | | FPQQPQQPF (γ-2) | (16) |
| | | IQPQQPAQL (γ-30) | (16) |
| | LMW-glutenin | FSQQQSPF (glt-156) | (16) |
| | | FSQQQQPL (glt-17) | (16) |
| | | QXPQQPQQF (glu-5) | (16) |

TABLE 6

List of different diploid, tetraploid and hexaploid wheat accessions used for screening of the presence of T cell stimulatory epitopes involved in CD. Only Arcade and Minaret have been on the market as commercially available varieties.

| Species (number in Figure) | Genome | Accession number | Country of origin | winter/spring type |
|---|---|---|---|---|
| Triticum monococcum (1) | AA | CGN 06602 | | |
| Triticum monococcum (2) | AA | CGN 10542 | | spring |
| Triticum speltoides (3) | SS, later mutated to BB | CGN 10682 | Israel | spring |
| Triticum speltoides (4) | SS, later mutated to BB | CGN 10684 | Turkey | spring |
| Triticum squarrosum (5) | DD | CGN 10719 | Israel | spring |
| Triticum squarrosum subsp. strangulata (6) | DD | CGN 10757 | Iran | spring |
| Triticum turgidum variety dicoccoides (7) | AABB | Rec. 965418 (1975) | Israel | winter |
| Triticum turgidum variety dicoccoides (8) | AABB | Rec. 965521 (1975) | Israel | winter |
| Triticum turgidum group carthlicum (9) | AABB | CGN 04221 | Iran | spring |
| Triticum turgidum group carthlicum (10) | AABB | CGN 08360 | Russia | spring |
| Triticum aestivum group aestivum (11) | AABBDD | CGN variety Arcade (1989) | Belgium | spring |
| Tritucum aestivum group aestivum (12) | AABBDD | CGN variety Minaret (1983) | The Netherlands | spring |
| Triticum aestivum group compactum (13) | AABBDD | CGN 04210 | Italy | spring |
| Triticum aestivum group compactum (14) | AABBDD | CGN 08315 | Switzerland | spring |
| Triticum aestivum (15) | AABBDD | CGN 08510 | | |
| Triticum aestivum (16) | AABBDD | CGN 12393 | | |

TABLE 7

Database analysis of gluten proteins for the presence of T cell stimulatory sequences involved in CD.

| | number of T cell stimulatory gluten sequences found in a single database entry | | | | | | | genes without T cell stimulatory sequences |
|---|---|---|---|---|---|---|---|---|
| | 0 | 1 | 2 | 3 | 4 | 5 | 6 or more | |
| α-gliadins | 10 | 7 | 7 | 2 | 1 | 0 | 2 | 10/29 (34%) |
| γ-gliadins | 0 | 1 | 1 | 10 | 3 | 0 | 2 | 0/17 (0%) |
| LMW-glutenin | 54 | 3 | 0 | 0 | 0 | 0 | 0 | 54/57 (95%) |
| HMW-glutenin | 1 | 5 | 5 | 4 | 3 | 3 | 3 | 1/22 (4.5%) |

TABLE 8

Overview of the results of screening of the different wheat accessions for the presence of T cell stimulatory epitopes involved in CD. Pepsin/trypsin digests of the different accessions were tested by the T cell based and mAb based assays.

| | | T cell assay | | | | | | mAb assay | | | |
|---|---|---|---|---|---|---|---|---|---|---|---|
| | Genome | Glia-α-2/9 | Glia-γ-30 | Glia-γ1 | LMW-Glt-156 | LMW-Glt-17 | HMW-glt | Glia-α-9 | Glia-γ-1 | LMW-Glt-156 | HMW-glt |
| 1 | AA | ++ | +++ | +++++ | ++ | +/− | + | +++ | +++ | ++++ | +/− |
| 2 | AA | +/− | + | +/− | +++++ | +/− | +/− | + | +++ | ++++ | +/− |
| 3 | SS/BB | +/− | +/− | +++ | ++ | ++++ | + | + | +/− | + | +/− |
| 4 | SS/BB | +/− | +/− | + | +/− | + | +/− | +/− | +/− | +/− | +/− |
| 5 | DD | ++++ | +++ | +++ | + | +++ | +++ | ++ | +++ | +/− | +/− |
| 6 | DD | +++ | +/− | + | +/− | ++ | ++ | +/− | ++ | +/− | +/− |
| 7 | AABB | + | ++ | ++ | ++++ | ++++ | +++ | +/− | ++ | ++ | + |
| 8 | AABB | + | +++++ | +++ | +++ | ++++ | ++++ | ++ | +++ | ++ | +++ |
| 9 | AABB | +/− | + | +/− | +++ | +++ | +++ | +/− | ++ | ++ | +++ |
| 10 | AABB | +++++ | ++++ | ++ | +++++ | +++++ | ++++ | ++++ | ++++ | ++++ | ++++ |

TABLE 8-continued

Overview of the results of screening of the different wheat accessions for the presence of T cell stimulatory epitopes involved in CD. Pepsin/trypsin digests of the different accessions were tested by the T cell based and mAb based assays.

| | Genome | T cell assay | | | | | | mAb assay | | | |
|---|---|---|---|---|---|---|---|---|---|---|---|
| | | Glia-α-2/9 | Glia-γ-30 | Glia-γ1 | LMW-Glt-156 | LMW-Glt-17 | HMW-glt | Glia-α-9 | Glia-γ-1 | LMW-Glt-156 | HMW-glt |
| 11 | AABBDD | + | + | + | +++ | +++ | + | +/− | + | ++ | +/− |
| 12 | AABBDD | + | +/− | ++ | +++ | +++ | ++ | +++ | +++ | +++ | ++ |
| 13 | AABBDD | + | +/− | +/− | + | + | +/− | − | + | + | +/− |
| 14 | AABBDD | +++ | +/− | ++ | ++ | +++ | ++ | ++++ | ++++ | ++++ | ++ |
| 15 | AABBDD | ++++ | ++++ | ++ | +++ | +++ | +++++ | ++ | +++ | ++ | ++++ |
| 16 | AABBDD | +/− | +/− | + | ++ | + | +++ | +/− | + | +++ | ++ |

(For the T cell assay the responses are represented relative to the maximum response given by the T cell clone indicated by +++++. Therefore +/− corresponds with <5%-; + corresponds with 5-20%-; ++ corresponds with 20-35%-; +++ corresponds with 35-65%-; ++++ corresponds with >65%, +++++ corresponds with 100% of the maximum response given by the T cell clone. For the mAb assay the amount of antigen detected is represented relative to the maximum amount (μg/ml) detected in a given accession indicated by ++++. Therefore +/− corresponds with <5%-, + corresponds with 5-10%-; ++ corresponds with 10-30%-; +++ corresponds with 30-60%; ++++ corresponds to 60-100% of the maximum amount of antigen measured in the mAb based competition assay)

LEGENDS

FIG. 1. Specificity of the mAb for the different T cell epitopes. Wells Of an Elisa plate were coated with 0.5 μg/ml peptides glia-α-2/9 (aa 59-71), glia-γ1 (aa 142-159) and LMW glutenin (aa 41-58) coupled to BSA. Next the plates were incubated with the anti-Glia-α-2/9 mAb (black bars), the anti-Glia-γ1 (hatched bars) and the anti-LMW glutenin (grey bars) mAb. Binding of the mAb was detected with a peroxidase coupled rabbit-anti-mouse polyclonal antibody and visualized with TMB.

FIG. 2. Schematic representation of a competition experiment. In a competition experiment the gluten containing sample (⊥) is mixed with a fixed concentration of biotinylated indicator peptide encoding a T cell stimulatory peptide (⟶★). This mixture was added to an Elisa plate previously coated with a mAb specific for the biotinylated indicator peptide. During the incubation, the T cell epitopes present in the sample compete with the biotinylated indicator peptide for binding to the mAb. After washing bound indicator peptide was visualized with peroxidase conjugated streptavidine and TMB.

Figure 3:
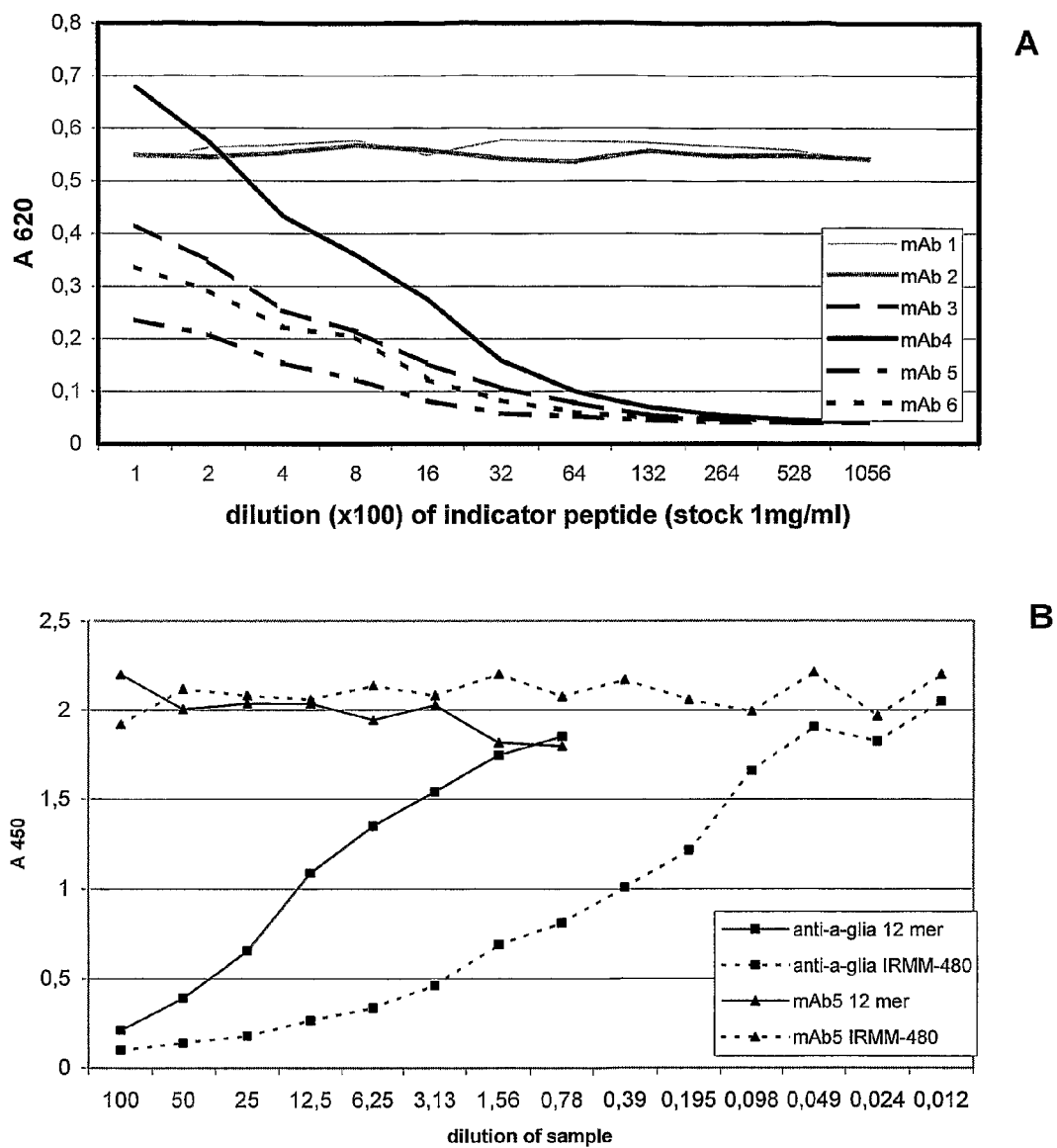
Figure 4:
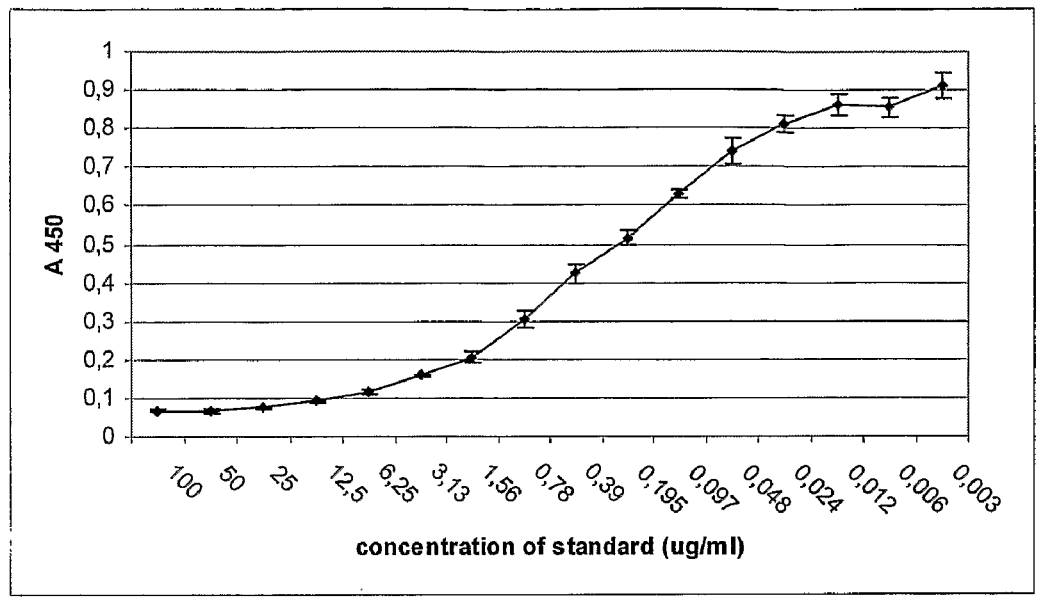
Figure 4:
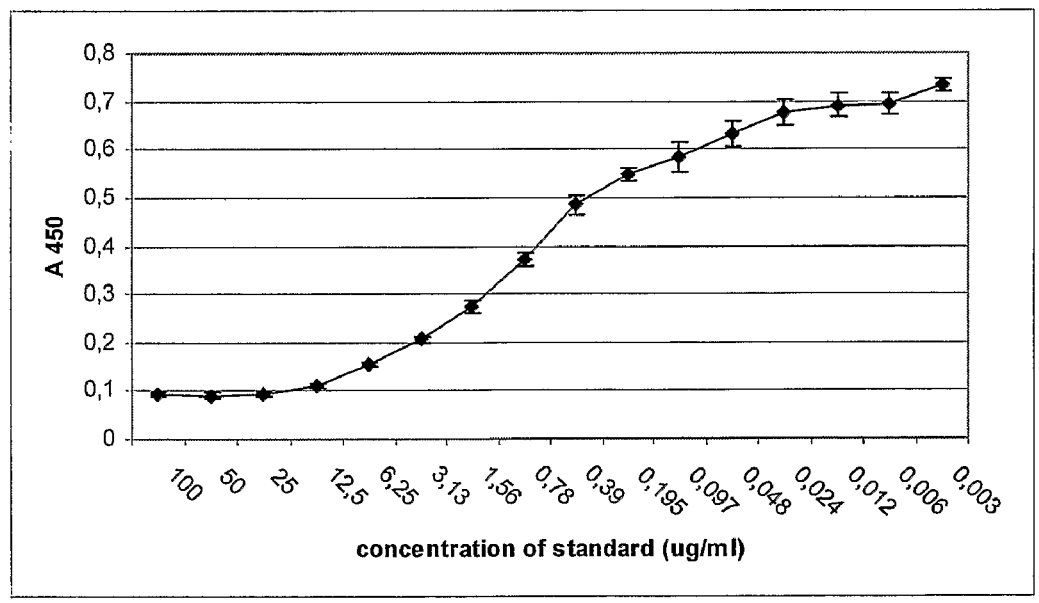

FIG. 3. Selection of mAb specific for detection of T cell stimulatory epitopes of α-gliadin that are suitable for competition experiments. (A) Experiment in which binding of the biotinylated indicator peptide by the immobilized mAb specific for the Gliaα2/9 T cell epitope was tested. MAb were coated to the Elisa plates and binding of different dilutions of the indicator peptide was visualised by streptavidin coupled HRP and TMB. (B) Competition assay for Glia-α2/α9 epitope using the anti-Glia-α2/9 and a mAb not suitable for its use in a competition assay. Competition of both a 12 mer peptide and the IRMM-480 standard containing intact proteins with the biotinylated indicator peptide was tested.

FIG. 4. Competition assay for the detection of different T cell stimulatory epitopes in gluten containing samples. (A) Competition assay for Glia-α2/α9 epitope (B) Competition assay for Glia-γ1 epitope. Dilutions of the European gliadin reference IRMM-480[26] were used as standard. Data represent the mean±SD of five experiments. The detection limit of the competition assay (defined as the concentration of standard showing an optical difference in absorbance compared to absorbance in the absence of the peptide) was 12 ng/ml for both the Glia-α2/9 epitope and the Glia-γ1 T cell epitope.

Figure 5:
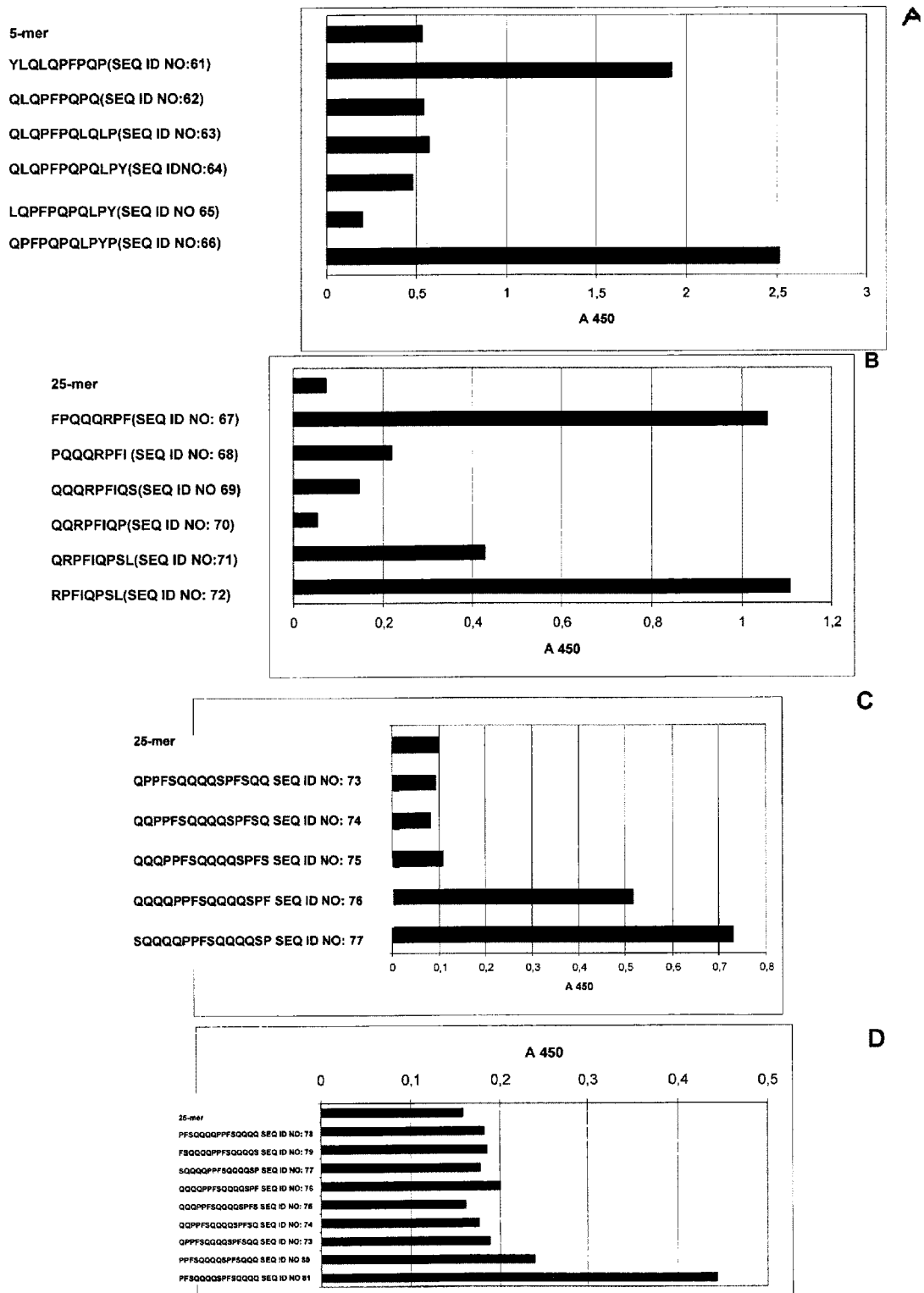

FIG. 5. Minimal epitope detected by (A) anti Glia-[alpha]-2/9 mAb, (B) the anti Glia-[gamma]1 mAb, (C) anti-LMW glutenin-1 mAb and (D) anti-LMW glutenin-2 mAb. The minimal epitope was determined by measuring the binding of the T cell epitope specific mAb to a set of overlapping peptides covering the entire T cell epitopes. The minimal epitope determined for the anti-Glia-[alpha]2/9 mAb is LQPFPQPQ (SEQ ID NO: 20)*, for the anti-Glia-[gamma]1 QQRPFI (SEQ ID NO: 4), for the anti-LMW glutenin-1 QSPFS (SEQ ID NO: 8) and for the anti-LMW glutenin-2 PPFSQQ (SEQ ID NO: 7).

*However since for the generation of the anti-Gliaα2/9 mAb the immunizations were performed with peptides with an aminohexanoyl group N-terminally pf proline, the minimal epitope is XQPFPQPQ (SEQ ID NO: 3).

Figure 6:
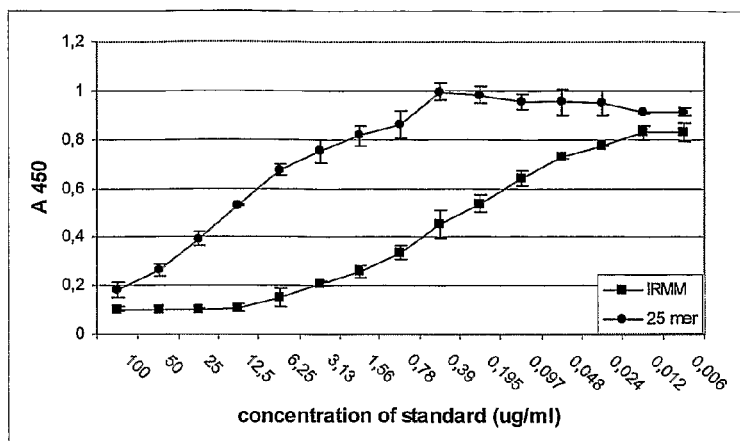
Figure 6:
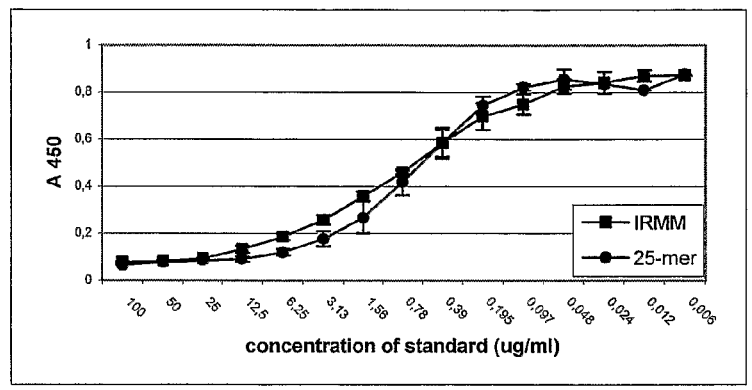
Figure 6:
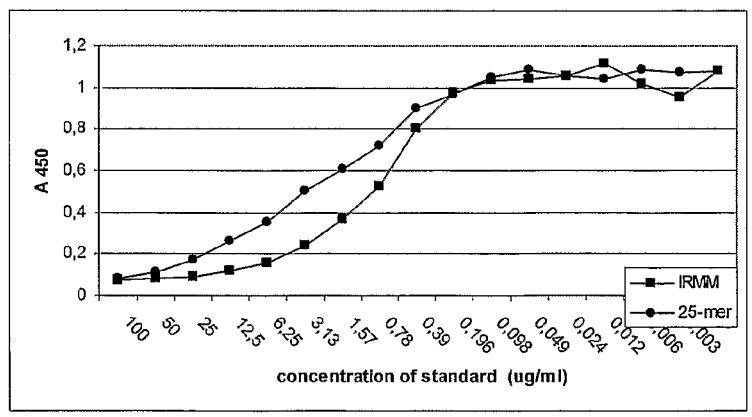
Figure 6:
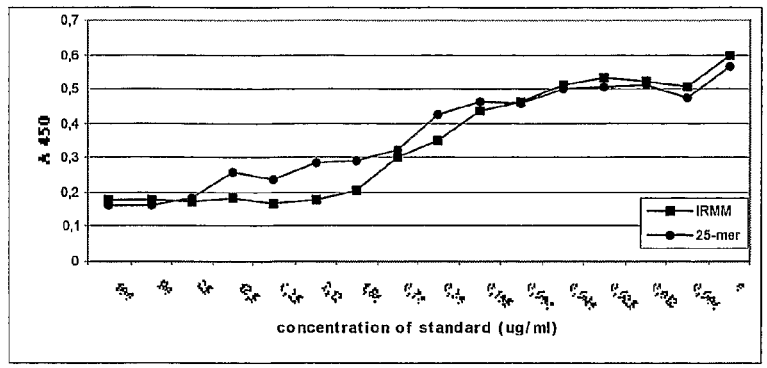

FIG. 6. Comparison of the affinity of the (A) anti-Glia-α2/9 mAb (B) anti-Glia-γ1 mAb (C) anti-LMW glutenin-1 mAb and (D) anti-LMW-glutenin-2 mAb for T cell epitopes encoded on intact proteins and peptides. Competition experiments were performed with both intact proteins (European gliadin reference) and a 25-mer synthetic peptide. Data represent the mean±SD of two experiments FIG. 7. Detection of T cell stimulatory epitopes Glia-α2/9 (black bars) and Glia-γ1 (hatched bars) and Glt-156 (grey bars) in protein preparations of different cereals by (A) the competition assay for Glia-α2/9 and Glia-γ1 and (B) a Glia-α2/9 specific T cell clone (C) a Glia-γ1 specific T cell clone and (D) the competition assay for Glt 156 using anti-LMW glutenin-1 mAb. Both the T cell clones and the competition assay detect peptides in barley, rye, triticale and oats Since the level of Glia-α2/9 epitopes detected by the competition assay in the barley preparation (315 μg/g) was very high compared to the levels in other cereals, the bar extends beyond the applied scale of the graph.

Figure 8:
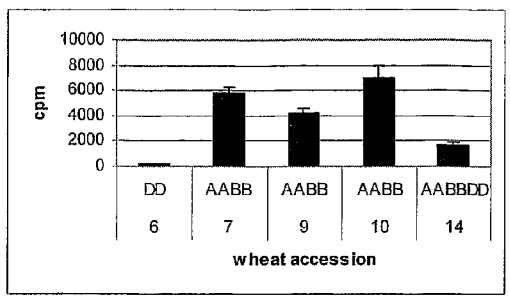
Figure 8:
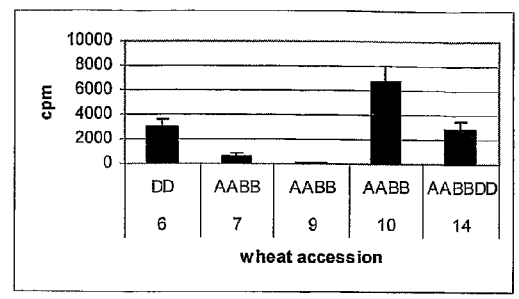
Figure 8:
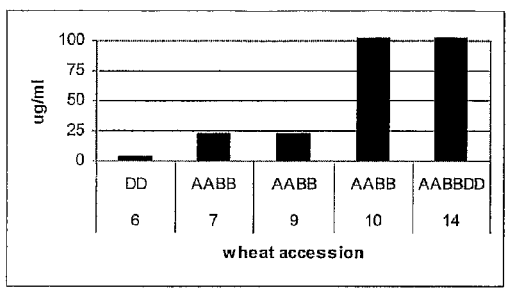
Figure 8:
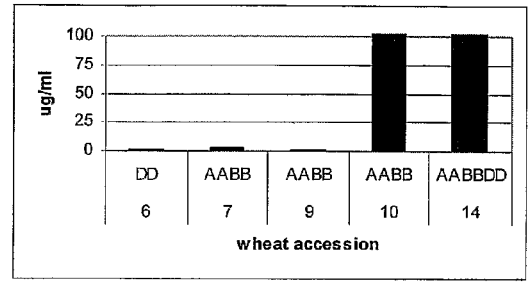
Figure 8:
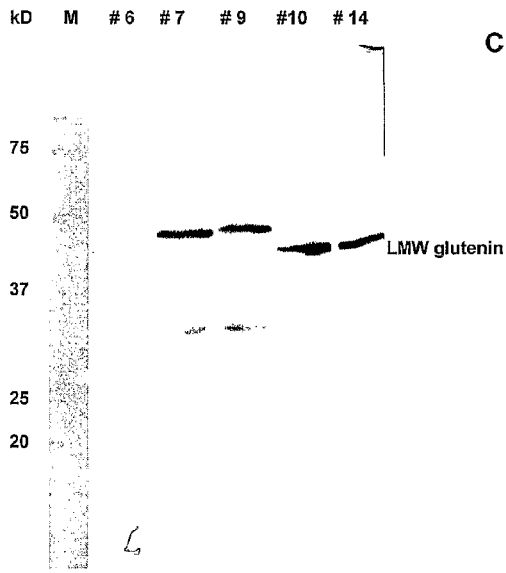
Figure 8:
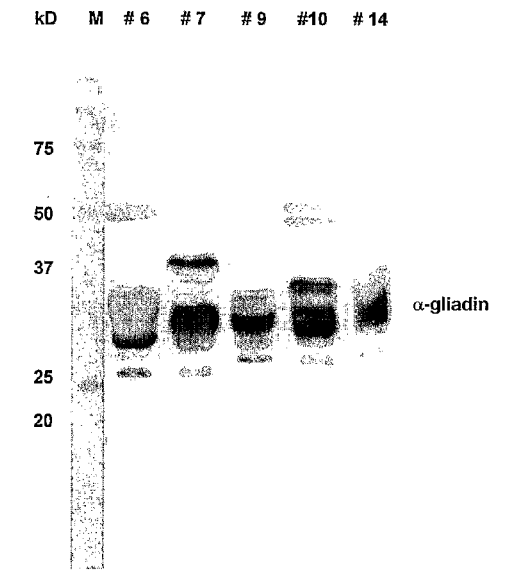

FIG. 8. Analysis of gluten proteins of Tritucum accessions with different levels of T cell stimulatory epitopes in the T cell assay (A and D) and mAb based competition assay (B and D). (A) Stimulation of the LMW-Glt-156 specific T cell clone, (B) mAb based competition assay specific for the LMW-Glt-156 T cell epitope, (C) Western blot stained with the anti-LMW-Glt-156 T cell epitope specific mAb, (D) Stimulation of the Glia-α2/9 specific T cell clone, (E) mAb based competition assay specific for the Glia-α9 T cell epitope, (1) Western blot stained with the anti-Glia-α9 T cell epitope specific mAb. The experiments displayed in panel A and D were performed in triplicate and the mean±SD of each measurement is shown.

Figure 9:
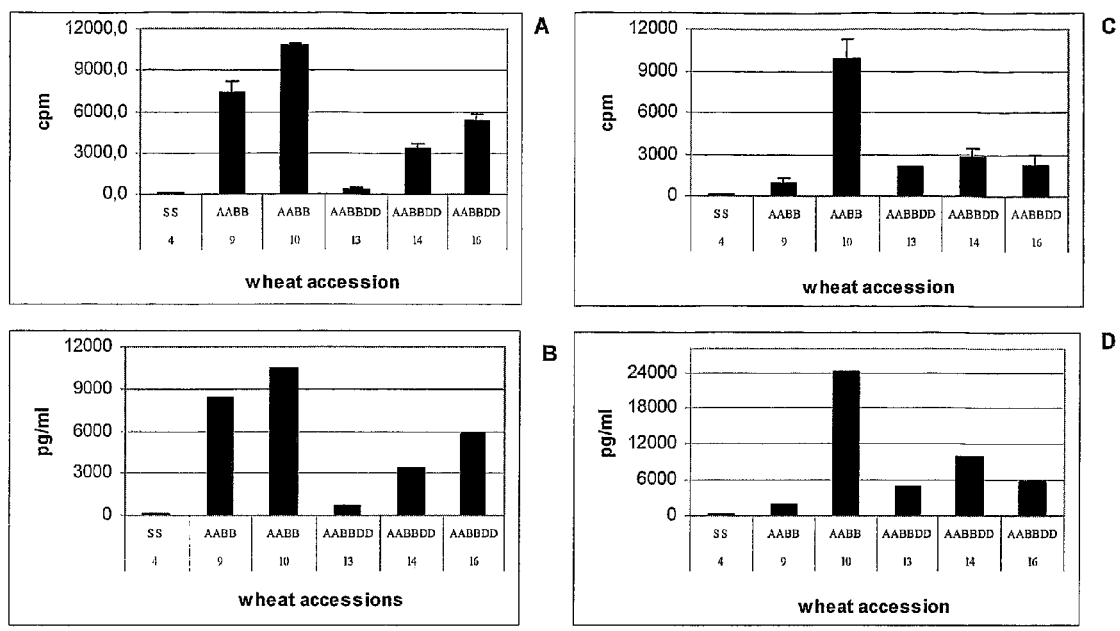

FIG. 9. Correlation between T cell proliferation and IFN-γ production after stimulation of T cell clones with protein extracts of six wheat accessions. Two T cell clones, specific for the gluten peptides LMW-Glt-156 (panel A and B) and Glia-α2/9 (panel C and D), were tested against protein extracts of six wheat accessions at a concentration of 2 μg/ml protein. T cell stimulation was determined by measurement of proliferation (panel A and C) and IFN-γ production (panel B and D). The experiments displayed in panel A and C were performed in triplicate and the mean±SD of each measurement is shown.

FIG. 10:

Detection of HMW-glutenin T cell epitope in different wheat accessions in a T cell assay (A) and in a mAb based competition assay (B). The T cell responses were defined as a stimulation index ([T+APC+antigen]/[T+APC]).

---

The invention claimed is:

1. A method for detecting gluten or gluten-like protein or a gluten derived peptidic residue in a sample comprising contacting said sample with an antibody that is specific for an amino acid sequence that is indicative for the presence of a T-cell epitope in the gluten or the gluten-like protein or the gluten derived peptidic residue and determining whether the antibody is bound to a target peptide in said sample, wherein the antibody comprises a sequence selected from the group consisting of SEQ ID NO:'s 40-49.

2. The method according to claim 1, wherein said T-cell epitope is an epitope presented by HLA-DQ-2.

3. The method according to claim 1, wherein determining the binding of the antibody comprises a competition assay.

4. The method according to claim 3, wherein binding of a competitor target to said antibody is detected.

5. The method according to claim 3, wherein said competition assay comprises measuring binding of a labelled peptide, wherein the labelled peptide is an analogue of the gluten or the gluten-like protein or the gluten derived peptidic residue.

6. The method according to claim 5, wherein said peptide is glia alpha 2/9.

7. The method according to claim 1, comprising an antibody comprising anti-alpha-gliadin heavy and light chain sequences SEQ ID NO: 40 and SEQ ID NO: 45.

8. The method according to claim 7, comprising at least two and preferably at least three antibodies comprising a sequence selected from the group consisting of SEQ ID NO:'s 40-49.

9. The method according to claim 1, further comprising quantitating the gluten or the gluten-like protein or the gluten derived peptidic residue in a quantitative assay.

10. The method according to claim 1, wherein said method is an ELISA assay or a dipstick test.

11. The method according to claim 1, wherein said sample comprises a precursor of a food stuff.

12. The method according to claim 11, wherein said sample is a hydrolysate of a cereal or food stuff.

13. The method according to claim 1, wherein said sample comprises a food stuff.

14. The method according to claim 1, wherein said sample comprises an intermediate product for a ready to consume food stuff.

15. The method according to claim 13, wherein said food stuff is ready for consumption.

16. The method according to claim 1, wherein said sample comprises protein from a cereal.

17. The method according to claim 16, further comprising modifying the cereal by genetic manipulation or producing progeny with said cereal.

18. The method according to claim 17, further comprising multiplying plant that said protein was derived from in the event that the T-cell epitope in the gluten or the gluten-like protein or the gluten derived peptidic residue was low or not detected in said sample.

19. The method according to claim 1, wherein said sample comprises teff.

20. The method according to claim 19, further comprising modifying teff by cross breeding and/or genetic manipulation.

* * * * *

UNITED STATES PATENT AND TRADEMARK OFFICE
CERTIFICATE OF CORRECTION

PATENT NO. : 7,993,869 B2
APPLICATION NO. : 11/630818
DATED : August 9, 2011
INVENTOR(S) : Drijfhout et al.

Page 1 of 2

It is certified that error appears in the above-identified patent and that said Letters Patent is hereby corrected as shown below:

In the Specifications:

Column 1, line 37:
Now reads: "high molecular weight (HMD)"
Should read: --high molecular weight (HMW)--

Column 1, line 51:
Now reads: "ppm of gliadines To further"
Should read: --ppm of gliadines. To further--

Column 3, line 63:
Now reads: "gliadin reference IRMM-480$^{2G}$ or"
Should read: --gliadin reference IRMM-480$^{26}$ or--

Column 13, line 11:
Now reads: "4°C in microliter plates"
Should read: --4°C in microtiter plates--

Column 13, line 17:
Now reads: "by 30 minutes (rain) incubation"
Should read: --by 30 minutes (min) incubation--

Signed and Sealed this
Twenty-first Day of May, 2013

Teresa Stanek Rea
*Acting Director of the United States Patent and Trademark Office*

Column 13, line 32:
Now reads: "Microliter plates (Nunc, Copenhagen"
Should read: --Microtiter plates (Nunc, Copenhagen--

Column 14, line 12:
Now reads: "recognizing the Glia-α1 T cell"
Should read: --recognizing the Glia-γ1 T cell--

Column 16, line 66:
Now reads: "detectable (α-gliadin) Also"
Should read: --detectable (α-gliadin). Also--

Column 17, line 1:
Now reads: "epitope could be detected Like"
Should read: --epitope could be detected. Like--

Column 22, line 53:
Now reads: "been considered 1.5 not to be"
Should read: --been considered not to be--

Column 28, after Table 2 please add the following paragraph:
Overview of peptides used in the competition assays for the detection of [alpha]- , [gamma]-gliadin, LMW glutenin and HMW-glutenin derived T cell stimulatory epitopes. (B= biotin, X = aminohexanoyl spacer)

Column 34, line 63:
Now reads: "epitope, (1) Western blot"
Should read: --epitope, (F) Western blot--